United States Patent [19]

Rainer et al.

[11] Patent Number: 4,686,230
[45] Date of Patent: * Aug. 11, 1987

[54] PICOLINE DERIVATIVE USEFUL AS GASTRIC ACID SECRETION INHIBITORS

[75] Inventors: Georg Rainer, Constance; Volker Figala, Allensbach; Bernhard Kohl, Constance, all of Fed. Rep. of Germany

[73] Assignee: Byk Gulden Lomberg Chemische Fabrik GmbH, Constance, Fed. Rep. of Germany

[ * ] Notice: The portion of the term of this patent subsequent to Nov. 26, 2002 has been disclaimed.

[21] Appl. No.: 794,230

[22] Filed: Oct. 29, 1985

[30] Foreign Application Priority Data

Oct. 31, 1984 [CH] Switzerland ............... 5235/84

[51] Int. Cl.$^4$ ............ C07D 403/12; A61K 31/44
[52] U.S. Cl. .................................. 514/338; 546/271
[58] Field of Search .................. 546/271; 514/338

[56] References Cited

U.S. PATENT DOCUMENTS 4,555,518 11/1985 Rainer ............................ 546/271
4,560,693 12/1985 Rainer ............................ 546/271

Primary Examiner—Jane T. Fan
Attorney, Agent, or Firm—Berman, Aisenberg & Platt

[57] ABSTRACT

Picoline derivatives of the formula I

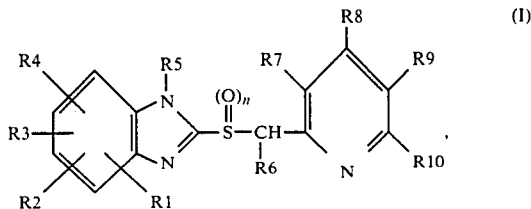

wherein the substituents have the meanings given in the description, and their salts are new compounds having a pronounced protective action on the stomach.

23 Claims, No Drawings

PICOLINE DERIVATIVE USEFUL AS GASTRIC ACID SECRETION INHIBITORS

RELATED APPLICATIONS

The subject matter disclosed and claimed in this application is related to that of each of the following applications:

(a) Application Ser. No. 606,872, filed May 1, 1984 (now U.S. Pat. No. 4,555,518), (b) Application Ser. No. 606,873, filed May 1, 1984 (now U.S. Pat. No. 4,560,693), and (c) Application Ser. No. 748,591, filed June 14, 1985.

FIELD OF APPLICATION OF THE INVENTION

The invention relates to new picoline derivatives, to processes for their preparation, to their use and to medicaments containing them. The compounds according to the invention are used in the pharmaceutical industry as intermediates and for the preparation of medicaments.

STATE OF THE ART

In European Patent Application No. 0,005,129, substituted pyridylsulphinylbenzimidazoles are described which are said to have properties inhibiting the secretion of gastric acid.—In European Patent Application No. 0,074,341, the use of a number of benzimidazole derivatives for the inhibition of the secretion of gastric acid is described.—In German Offenlegungsschrift No. 3,404,610, further benzimidazole derivatives are described as cell-protecting agents for the gastro-intestinal tract and as inhibitors for the secretion of gastric acid in mammals.

It has now been found, surprisingly, that the picoline derivatives, described in more detail below, have interesting and unexpected properties in which they differ in an advantageous manner from the known compounds.

DESCRIPTION OF THE INVENTION

The invention relates to novel picoline derivatives of the formula I

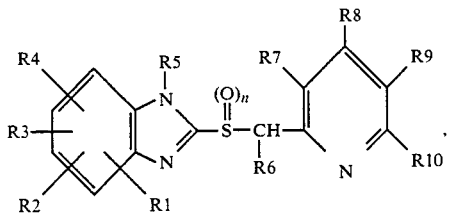

wherein
R1, R2, R3 and R4 can be in any desired positions in the benzo part of the benzimidazole and wherein R1 denotes hydrogen or $C_1$-$C_6$-alkyl, R2 denotes hydrogen, halogen, $C_1$-$C_6$-alkyl, $C_1$-$C_6$-alkoxy, $C_1$-$C_4$-alkoxy-$C_1$-$C_4$-alkyl, $C_1$-$C_4$-alkoxy-$C_1$-$C_4$-alkoxy, phenyl, phenoxy, phenoxy-$C_1$-$C_4$-alkyl, phenoxy-$C_1$-$C_4$-alkoxy, phen-$C_1$-$C_4$-alkyl or phen-$C_1$-$C_4$-alkoxy, R3 dentoes hydrogen, $C_1$-$C_6$-alkyl, $C_1$-$C_6$-alkoxy, $C_1$-$C_4$-alkoxy wholly or predominantly substituted by fluorine, chlorodifluoromethoxy or 2-chloro-1,1,2-trifluoroethoxy or, together with R4, denotes $C_1$-$C_2$-alkylenedioxy wholly or partially substituted by fluorine, or chlorotrifluoroethylenedioxy, R4 denotes $C_1$-$C_4$-alkoxy wholly or predominantly substituted by fluorine, chlorodifluoromethoxy or 2-chloro-1,1,2-trifluoroethoxy or, together with R3, denotes $C_1$-$C_2$-alkylenedioxy wholly or partially substituted by fluorine, or chlorotrifluoroethylenedioxy, R5 denotes hydrogen or a group which can readily be eliminated under physiological conditions, R6 denotes hydrogen or $C_1$-$C_4$-alkyl, R7 denotes hydrogen, $C_1$-$C_6$-alkyl or $C_1$-$C_6$-alkoxy, R8 denotes hydrogen, $C_1$-$C_6$-alkyl, $C_1$-$C_6$-alkoxy, $C_1$-$C_4$-alkoxy-$C_1$-$C_4$-alkoxy, $C_2$-$C_5$-alkenyloxy or $C_2$-$C_5$-alkynyloxy, R9 denotes hydrogen, $C_1$-$C_6$-alkyl or $C_1$-$C_6$-alkoxy, R10 denotes hydrogen or $C_1$-$C_6$-alkyl and n represents the numbers 0 or 1, and the salts of these compounds, with the proviso that a substituent R1, R2 or R3 in the 5- or 6-position in the benzimidazole cannot have the meanings of hydrogen, halogen, $C_1$-$C_6$-alkyl, $C_1$-$C_6$alkoxy, $C_1$-$C_4$-alkoxy wholly or predominantly substituted by fluorine, chlorodifluoromethoxy or, together with R4—if this is in the 6- or 5-position—$C_1$-$C_2$-alkylenedioxy wholly or partially sutstituted by fluorine, or chlorotrifluoroethylenedioxy, if R4 is in the 6- or 5-position and denotes $C_1$-$C_4$-alkoxy wholly or predominantly substituted by fluorine or chlorodifluoromethoxy or, together with R3—if this is in the 5- or 6-position—$C_1$-$C_2$-alkylenedioxy wholly or partially substituted by fluorine, or chlorotrifluoroethylenedioxy and R5 denotes hydrogen and R6 denotes hydrogen and R7 denotes hydrogen or $C_1$-$C_6$-alkyl or $C_1$-$C_6$-alkoxy and R8 denotes hydrogen or $C_1$-$C_6$-alkyl or $C_1$-$C_6$-alkoxy and R9 denotes hydrogen or $C_1$-$C_6$-alkyl or $C_1$-$C_6$-alkoxy and R10 denotes hydrogen, and hydrogen atoms are present in the 4- and 7-positions of the benzimidazole.

Halogen within the meaning of the present invention is bromine, chlorine and especially fluorine.

$C_1$-$C_6$-Alkyl represents straight-chain and branched alkyl radicals. Straight-chain alkyl radicals are the hexyl, pentyl, butyl, propyl, ethyl and especially the methyl radical. Examples of branched alkyl radicals are the neopentyl, i-butyl, sec.-butyl, t-butyl and isopropyl radicals.

$C_1$-$C_6$-Alkoxy represents straight-chain or branched alkoxy radicals. The hexyloxy, neopentyloxy, butoxy, i-butoxy, sec.-butoxy, t-butoxy, propoxy, isopropoxy, ethoxy and especially methoxy radical may be mentioned as examples.

$C_1$-$C_4$-Alkoxy represents straight-chain or branched alkoxy radicals; the butoxy, i-butoxy, sec.-butoxy, t-butoxy, propoxy, isopropoxy, ethoxy and especially the methoxy radical may be mentioned as examples.

$C_1$-$C_4$-Alkyl represents straight-chain or branched alkyl radicals; the butyl, i-butyl, sec.-butyl, t-butyl, propyl, isopropyl, ethyl and especially the methyl radical may be mentioned as examples.

$C_1$-$C_4$-Alkoxy-$C_1$-$C_4$-alkyl represents $C_1$-$C_4$-alkyl which is substituted by $C_1$-$C_4$-alkoxy. The ethoxymethyl, propoxybutyl, methoxymethyl and especially the methoxyethyl and ethoxyethyl radicals may be mentioned as examples.

$C_1$-$C_4$-Alkoxy-$C_1$-$C_4$-alkoxy represents $C_1$-$C_4$-alkoxy which is substituted by $C_1$-$C_4$-alkoxy. The methoxypropoxy, ethoxymethoxy and especially the ethoxyethoxy and methoxyethoxy radical may be mentioned as examples.

Phenoxy-$C_1$-$C_4$-alkyl represents $C_1$-$C_4$-alkyl which is substituted by a phenoxy radical. The phenoxypropyl and phenoxyethyl radicals may be mentioned as examples.

Phenoxy-$C_1$-$C_4$-alkoxy represents $C_1$-$C_4$-alkoxy which is substituted by a phenoxy radical. The phenoxyethoxy and phenoxypropoxy radicals may be mentioned as examples.

Phen-$C_1$-$C_4$-alkyl represents $C_1$-$C_4$-alkyl which is substituted by a phenyl radical. The phenethyl and especially the benzyl radical may be mentioned as examples.

Phen-$C_1$-$C_4$-alkoxy represents $C_1$-$C_4$-alkoxy which is substituted by a phenyl radical. The 2-phenyl-ethoxy and benzyloxy radicals may be mentioned as examples.

The 1,1,2-trifluoroethoxy, perfluoropropoxy, perfluoroethoxy radicals and especially the 1,1,2,2-tetrafluoroethoxy, trifluoromethoxy, 2,2,2-trifluoroethoxy and difluoromethoxy radicals may be mentioned as examples of $C_1$-$C_4$-alkoxy wholly or predominantly substituted by fluorine.

The 1,1-difluoroethylenedioxy (—O—$CF_2$—$CH_2$—O—), 1,1,2,2-tetrafluoroethylenedioxy (—O—$CF_2$—$CF_2$—O—) and especially the difluoromethylenedioxy (—O—$CF_2$—O—) and 1,1,2-trifluoroethylenedioxy (—O—$CF_2$—CHF—O—) radicals may be mentioned as examples of $C_1$-$C_2$-alkylenedioxy wholly or partially substituted by fluorine.

The group R5 which can be readily eliminated under physiological conditions is a substituent which is separated by hydrolysis—if appropriate with enzymatic catalysis—from the nitrogen atom with formation of an N—H bond, the substituent itself being converted—with bonding to a hydroxyl group—into a physiologically acceptable and in particular pharmacologically tolerated compound. As the groups R5 which can be eliminated, especially all types of substituted carbonyl groups may be mentioned, such as the alkylcarbonyl, arylcarbonyl, aralkylcarbonyl, alkoxycarbonyl, aryloxycarbonyl, aralkoxycarbonyl or substituted or unsubstituted carbamoyl groups may be mentioned. The methoxycarbonyl, t-butoxycarbonyl, benzoyl, phenylcarbamoyl and dimethylcarbamoyl groups may be mentioned as examples.

$C_2$-$C_5$-Alkenyloxy represents alkenyloxy radicals, such as the pent-2-enyloxy, but-1-enyloxy and especially the allyloxy radical.

$C_2$-$C_5$-Alkynyloxy represents alkynyloxy radicals, such as the ethynyloxy and especially the prop-2-ynyloxy radical.

Possible salts of compounds of the formula I, in which n denotes the number 0 (sulphides), preferably are all acid addition salts. The pharmacologically acceptable salts of the inorganic and organic acids usually employed in pharmacy may be mentioned in particular. Pharmacologically unacceptable salts which may initially be obtained, for example, as process products when the compounds according to the invention are prepared on an industrial scale are converted into pharmacologically acceptable salts by processes which are known to those skilled in the art. Examples of suitable salts of this type are water-soluble and water-insoluble acid addition salts, such as the hydrochloride, hydrobromide, hydriodide, phosphate, nitrate, sulphate, acetate, citrate, gluconate, benzoate, hibenzate, fendizoate, butyrate, sulphosalicylate, maleate, laurate, malate, fumarate, succinate, oxalate, tartrate, amsonate, embonate, metemebonate, stearate, tosylate, 2-hydroxy-3-naphthoate, 3-hydroxy-2-naphthoate or mesylate.

Possible salts of the compounds of the formula I, in which n denotes the number 1 (sulphoxides), preferably are basic salts, in particular pharmacologically acceptable salts with inorganic and organic bases usually employed in pharmacy. Lithium, sodium, potassium, calcium, aluminium, magnesium, titanium, ammonium or guanidinium salts may be mentioned as examples of basic salts.

If R3 and R4 together denote $C_1$-$C_2$-alkylenedioxy wholly or partially substituted by fluorine or chlorotrifluoroethylenedioxy, the substituents R3 and R4 are bonded in neighbouring positions to the benzo part of the benzimidazole ring.

One aspect of the invention are compounds of the formula I
wherein
R1, R2, R3 and R4 can be in any desired positions in the benzo part of the benzimidazole and wherein
R1 denotes hydrogen or $C_1$-$C_6$-alkyl,
R2 denotes hydrogen, halogen, $C_1$-$C_6$-alkyl, $C_1$-$C_6$-alkoxy, $C_1$-$C_4$-alkoxy-$C_1$-$C_4$-alkyl, $C_1$-$C_4$-alkoxy-$C_1$-$C_4$-alkoxy, phenyl, phenoxy, phenoxy-$C_1$-$C_4$-alkyl, phenoxy-$C_1$-$C_4$-alkoxy, phen-$C_1$-$C_4$-alkyl or phen-$C_1$-$C_4$-alkoxy,
R3 denotes hydrogen, $C_1$-$C_6$-alkyl, $C_1$-$C_6$-alkoxy, $C_1$-$C_4$-alkoxy wholly or predominantly substituted by fluorine, chlorodifluoromethoxy or 2-chloro-1,1,2-trifluorethoxy or, together with R4, denotes $C_1$-$C_2$-alkylenedioxy wholly or partially substituted by fluorine, or chlorotrifluoroethylenedioxy,
R4 denotes $C_1$-$C_4$-alkoxy wholly or predominantly substituted by fluorine, chlorodifluoromethoxy or 2-chloro-1,1,2-trifluoroethoxy or, together with R3, denotes $C_1$-$C_2$-alkylenedioxy wholly or partially substituted by fluorine, or chlorotrifluoroethylenedioxy,
R5 denotes hydrogen or a group which can readily be eliminated under physiological conditions,
R6 denotes hydrogen or $C_1$-$C_4$-alkyl,
R7 denotes hydrogen or $C_1$-$C_6$-alkyl,
R8 denotes hydrogen, $C_1$-$C_6$-alkyl, $C_1$-$C_6$-alkoxy, $C_1$-$C_4$-alkoxy-$C_1$-$C_4$-alkoxy, $C_2$-$C_5$-alkenyloxy or $C_2$-$C_5$-alkynyloxy,
R9 denotes hydrogen or $C_1$-$C_6$-alkyl,
R10 denotes hydrogen or $C_1$-$C_6$-alkyl and
n represents the numbers 0 or 1,
and the salts of these compounds, with the proviso that a substituent R1, R2 or R3 in the 5- or 6-position in the benzimidazole cannot have the meanings of
hydrogen, halogen, $C_1$-$C_6$-alkyl, $C_1$-$C_6$-alkoxy, $C_1$-$C_4$-alkoxy wholly or predominantly substituted by fluorine, chlorodifluoromethoxy or, together with R4—if this is in the 6- or 5-position—$C_1$-$C_2$-alkylenedioxy wholly or partially substituted by fluorine, or chlorotrifluoroethylenedioxy, if
R4 is in the 6- or 5-position and denotes $C_1$-$C_4$-alkoxy wholly or predominantly substituted by fluorine or chlorodifluoromethoxy or, together with R3—if this is in the 5- or 6-position—$C_1$-$C_2$-alkylenedioxy wholly or partially substituted by fluorine, or chlorotrifluoroethylenedioxy and
R5 denotes hydrogen and
R6 denotes hydrogen and
R7 denotes hydrogen or $C_1$-$C_6$-alkyl and R8 denotes hydrogen or $C_1$–$C_6$-alkyl or $C_1$–$C_6$-alkoxy and R9 denotes hydrogen or $C_1$–$C_6$-alkyl and R10 denotes hydrogen, and hydrogen atoms are present in the 4- and 7-positions of the benzimidazole.

A further aspect of the invention are compounds of the formula I,
wherein

R1, R2, R3 and R4 can be in any desired positions in the benzo part of the benzimidazole and wherein R1 denotes hydrogen or $C_1$–$C_6$-alkyl, R2 denotes hydrogen, halogen, $C_1$–$C_6$-alkyl, $C_1$–$C_6$-alkoxy, $C_1$–$C_4$-alkoxy-$C_1$–$C_4$-alkyl, $C_1$–$C_4$-alkoxy-$C_1$–$C_4$-alkoxy, phenyl, phenoxy, phenoxy-$C_1$–$C_4$-alkyl, phenoxy-$C_1$–$C_4$-alkoxy, phen-$C_1$–$C_4$-alkyl or phen-$C_1$–$C_4$-alkoxy, R3 denotes hydrogen, $C_1$–$C_6$-alkyl, $C_1$–$C_6$-alkoxy $C_1$–$C_4$-alkoxy wholly or predominantly substituted by fluorine, chlorodifluoromethoxy or 2-chloro-1,1,2-trifluoroethoxy or, together with R4, denotes $C_1$–$C_2$-alkylenedioxy wholly or partially substituted by fluorine, or chlorotrifluoroethylenedioxy, R4 denotes $C_1$–$C_4$-alkoxy wholly or predominantly substituted by fluorine, chlorodifluoromethoxy or 2-chloro-1,1,2-trifluoroethoxy or, together with R3, denotes $C_1$–$C_2$-alkylenedioxy wholly or partially substituted by fluorine, or chlorotrifluoroethylenedioxy, R5 denotes hydrogen or a group which can readily be eliminated under physiological conditions, R6 denotes hydrogen or $C_1$–$C_4$-alkyl, R8 denotes hydrogen, $C_1$–$C_6$-alkyl, $C_1$–$C_6$-alkoxy, $C_1$–$C_4$-alkoxy-$C_1$–$C_4$-alkoxy, $C_2$–$C_5$-alkenyloxy or $C_2$–$C_5$-alkynyloxy, one of the substituents R7 and R9 denotes $C_1$–$C_6$-alkoxy and the other denotes hydrogen, $C_1$–$C_6$-alkyl or $C_1$–$C_6$-alkoxy, R10 denotes hydrogen or $C_1$–$C_6$-alkyl and n represents the numbers 0 or 1, and the salts of these compounds, with the proviso that a substituent R1, R2 or R3 in the 5- or 6-position in the benzimidazole cannot have the meanings of hydrogen, halogen, $C_1$–$C_6$-alkyl, $C_1$–$C_6$-alkoxy, $C_1$–$C_4$-alkoxy wholly or predominantly substituted by fluorine, chlorodifluoromethoxy or, together with R4—if this is in the 6- or 5-position—$C_1$–$C_2$-alkylenedioxy wholly or partially substituted by fluorine, or chlorotrifluoroethylenedioxy, if R4 is in the 6- or 5-position and denotes $C_1$–$C_4$-alkoxy wholly or predominantly substituted by fluorine or chlorodifluoromethoxy or, together with R3—if this is in the 5- or 6-position—$C_1$–$C_2$-alkylenedioxy wholly or partially substituted by fluorine, or chlorotrifluoroethylenedioxy and R5 denotes hydrogen and R6 denotes hydrogen and R8 denotes hydrogen or $C_1$–$C_6$-alkyl or $C_1$–$C_6$-alkoxy and one of the substituents R7 and R9 denotes $C_1$–$C_6$-alkoxy and the other denotes hydrogen or $C_1$–$C_6$-alkyl or $C_1$–$C_6$-alkoxy and R10 denotes hydrogen, and hydrogen atoms are present in the 4- and 7-positions of the benzimidazole.

One embodiment (embodiment a) of the invention comprises compounds of the formula I, wherein R6 denotes hydrogen and R10 denotes hydrogen, and R1, R2, R3, R4, R5, R7, R8, R9 and n have the meanings given above, and their salts.

A further embodiment (embodiment b) of the invention comprises compounds of the formula I, wherein R6 denotes $C_1$–$C_4$-alkyl and R10 denotes hydrogen, and R1, R2, R3, R4, R5, R7, R8, R9 and n have the meanings given above, and their salts.

Compounds according to the invention which should be singled out are those of the formula I in which R1 denotes hydrogen or $C_1$–$C_4$-alkyl, R2 denotes hydrogen, halogen, $C_1$–$C_4$-alkyl, $C_1$–$C_4$-alkoxy, $C_1$–$C_4$-alkoxy-$C_1$–$C_4$-alkyl, $C_1$–$C_4$-alkoxy-$C_1$–$C_4$-alkoxy, phenyl, phenoxy, phenoxy-$C_1$–$C_4$-alkyl, phenoxy-$C_1$–$C_4$-alkoxy, phen-$C_1$–$C_4$-alkyl or phen-$C_1$–$C_4$-alkoxy, R3 denotes hydrogen, $C_1$–$C_4$-alkyl, $C_1$–$C_4$-alkoxy, $C_1$–$C_4$-alkoxy wholly or predominantly substituted by fluorine, chlorodifluoromethoxy, 2-chloro-1,1,2-trifluoroethoxy or, together with R4, denotes $C_1$–$C_2$-alkylenedioxy wholly or partially substituted by fluorine, or chlorotrifluoroethylenedioxy, R4 denotes $C_1$–$C_4$-alkoxy wholly or predominantly substituted by fluorine, chlorodifluoromethoxy, 2-chloro-1,1,2-trifluoroethoxy or, together with R3, denotes $C_1$–$C_2$-alkylenedioxy wholly or partially substituted by fluorine, or chlorotrifluoroethylenedioxy, R5 denotes hydrogen, R6 denotes hydrogen or $C_1$–$C_4$-alkyl, R7 denotes hydrogen, $C_1$–$C_4$-alkyl or $C_1$–$C_4$-alkoxy, R8 denotes hydrogen, $C_1$–$C_4$-alkyl, $C_1$–$C_4$-alkoxy, $C_1$–$C_4$-alkoxy-$C_1$–$C_4$-alkoxy, $C_2$–$C_5$-alkenyloxy or $C_2$–$C_5$-alkynyloxy, R9 denotes hydrogen, $C_1$–$C_4$-alkyl or $C_1$–$C_4$-alkoxy, R10 denotes hydrogen or $C_1$–$C_4$-alkyl and n represents the numbers 0 or 1, and the salts of these compounds, with the proviso that the substituents R1, R2 or R3 in the 5- or 6-position in the benzimidazole cannot have the meanings of hydrogen, halogen, $C_1$–$C_4$-alkyl, $C_1$–$C_4$-alkoxy, $C_1$–$C_4$-alkoxy wholly or predominantly substituted by fluorine, chlorodifluoromethoxy or, together with R4—if this in the 6- or 5-position—$C_1$–$C_2$-alkylenedioxy wholly or partially substituted by fluorine or chlorotrifluoroethylenedioxy, if R4 is in the 6- or 5-position and denotes $C_1$–$C_4$-alkoxy wholly or predominantly substituted by fluorine or chlorodifluoromethoxy or, together with R3—if this is in the 5- or 6-position—denotes $C_1$–$C_2$-alkylenedioxy wholly or partially substituted by fluorine, or chlorotrifluoroethylenedioxy and R5 denotes hydrogen and R6 denotes hydrogen and R7 denotes hydrogen or $C_1$–$C_4$-alkyl or $C_1$–$C_4$-alkoxy and R8 denotes hydrogen or $C_1$–$C_4$-alkyl or $C_1$–$C_4$-alkoxy and R9 denotes hydrogen or $C_1$–$C_4$-alkyl or $C_1$–$C_4$-alkoxy and R10 denotes hydrogen, and hydrogen atoms are present in the 4- and 7-positions of the benzimidazole.

One aspect of the compounds according to the invention which should be singled out are those of the formula I
wherein R1 denotes hydrogen or $C_1$–$C_4$-alkyl, R2 denotes hydrogen, halogen, $C_1$-$C_4$-alkyl, $C_1$-$C_4$-alkoxy, $C_1$-$C_4$-alkoxy-$C_1$-$C_4$-alkyl, $C_1$-$C_4$-alkoxy-$C_1$-$C_4$-alkoxy, phenyl, phenoxy, phenoxy-$C_1$-$C_4$-alkyl, phenoxy-$C_1$-$C_4$-alkoxy, phen-$C_1$-$C_4$-alkyl or phen-$C_1$-$C_4$-alkoxy, R3 denotes hydrogen, $C_1$-$C_4$-alkyl, $C_1$-$C_4$-alkoxy, $C_1$-$C_4$-alkoxy wholly or predominantly substituted by fluorine, chlorodifluoromethoxy, 2-chloro-1,1,2-trifluoroethoxy or, together with R4, denotes $C_1$-$C_2$-alkylenedioxy wholly or partially substituted by fluorine, or chlorotrifluoroethylenedioxy, R4 denotes $C_1$-$C_4$-alkoxy wholly or predominantly substituted by fluorine, chlorodifluoromethoxy, 2-chloro-1,1,2-trifluoroethoxy or, together with R3, denotes $C_1$-$C_2$-alkylenedioxy wholly or partially substituted by fluorine, or chlorotrifluoroethylenedioxy, R5 denotes hydrogen,
R6 denotes hydrogen or $C_1$-$C_4$-alkyl,
R7 denotes hydrogen or $C_1$-$C_4$-alkyl,
R8 denotes hydrogen, $C_1$-$C_4$-alkyl, $C_1$-$C_4$-alkoxy, $C_1$-$C_4$-alkoxy-$C_1$-$C_4$-alkoxy, $C_2$-$C_5$-alkenyloxy or $C_2$-$C_5$-alkynyloxy,
R9 denotes hydrogen or $C_1$-$C_4$-alkyl,
R10 denotes hydrogen or $C_1$-$C_4$-alkyl and
n represents the numbers 0 or 1, and
the salts of these compounds, with the proviso that the substituents R1, R2 or R3 in the 5- or 6-position in the benzimidazole cannot have the meanings of hydrogen, halogen, $C_1$-$C_4$-alkyl, $C_1$-$C_4$-alkoxy, $C_1$-$C_4$-alkoxy wholly or predominantly substituted by fluorine, chlorodifluoromethoxy or, together with R4—if this is in the 6- or 5-position—$C_1$-$C_2$-alkylenedioxy wholly or partially substituted by fluorine, or chlorotrifluoroethylenedioxy, if R4 is in the 6- or 5-position and denotes $C_1$-$C_4$-alkoxy wholly or predominantly substituted by fluorine, or chlorodifluoromethoxy or, together with R3—if this is in the 5- or 6-position—denotes $C_1$-$C_2$-alkylenedioxy wholly or partially substituted by fluorine, or chlorotrifluoroethylenedioxy and R5 denotes hydrogen and
R6 denotes hydrogen and
R7 denotes hydrogen or $C_1$-$C_4$-alkyl and
R8 denotes hydrogen or $C_1$-$C_4$-alkyl or $C_1$-$C_4$-alkoxy and
R9 denotes hydrogen or $C_1$-$C_4$-alkyl and
R10 denotes hydrogen,
and hydrogen atoms are present in the 4- and 7-positions of the benzimidazole.

A further aspect of the compounds according to the invention which should be singled out are those wherein R1 denotes hydrogen or $C_1$-$C_4$-alkyl,
R2 denotes hydrogen, halogen, $C_1$-$C_4$-alkyl, $C_1$-$C_4$-alkoxy, $C_1$-$C_4$-alkoxy-$C_1$-$C_4$-alkyl, $C_1$-$C_4$-alkoxy-$C_1$-$C_4$-alkoxy, phenyl, phenoxy, phenoxy-$C_1$-$C_4$-alkyl, phenoxy-$C_1$-$C_4$-alkoxy, phen-$C_1$-$C_4$-alkyl or phen-$C_1$-$C_4$-alkoxy,
R3 denotes hydrogen, $C_1$-$C_4$-alkyl, $C_1$-$C_4$-alkoxy, $C_1$-$C_4$-alkoxy wholly or predominantly substituted by fluorine, chlorodifluoromethoxy, 2-chloro-1,1,2-trifluoroethoxy or, together with R4, denotes $C_1$-$C_2$-alkylenedioxy wholly or partially substituted by fluorine, or chlorotrifluoroethylenedioxy,
R4 denotes $C_1$-$C_4$-alkoxy wholly or predominantly substituted by fluorine, chlorodifluoromethoxy, 2-chloro-1,1,2-trifluoroethoxy or, together with R3, denotes $C_1$-$C_2$-alkylenedioxy wholly or partially substituted by fluorine, or chlorotrifluoroethylenedioxy,
R5 denotes hydrogen,
R6 denotes hydrogen or $C_1$-$C_4$-alkyl,
R8 denotes hydrogen, $C_1$-$C_4$-alkyl, $C_1$-$C_4$-alkoxy, $C_1$-$C_4$-alkoxy-$C_1$-$C_4$-alkoxy, $C_2$-$C_5$-alkenyloxy or $C_2$-$C_5$-alkynyloxy,
one of the substituents R7 and R9 denotes $C_1$-$C_4$-alkoxy and the other denotes hydrogen, $C_1$-$C_4$-alkyl or $C_1$-$C_4$-alkoxy,
R10 denotes hydrogen or $C_1$-$C_4$-alkyl and
n represents the numbers 0 or 1, and
the salts of these compounds, with the proviso that the substituents R1, R2 or R3 in the 5- or 6-position in the benzimidazole cannot have the meanings of hydrogen, halogen, $C_1$-$C_4$-alkyl, $C_1$-$C_4$-alkoxy, $C_1$-$C_4$-alkoxy wholly or predominantly substituted by fluorine, chlorodifluoromethoxy or, together with R4—if this is in the 6- or 5-position—$C_1$-$C_2$-alkylenedioxy wholly or partially substituted by fluorine, or chlorotrifluoroethylenedioxy, if R4 is in the 6- or 5-position and denotes $C_1$-$C_4$-alkoxy wholly or predominantly substituted by fluorine or chlorodifluoromethoxy or, together with R3—if this is in the 5- or 6-position—denotes $C_1$-$C_2$-alkylenedioxy wholly or partially substituted by fluorine, or chlorotrifluoroethylenedioxy and R5 denotes hydrogen and
R6 denotes hydrogen and
R8 denotes hydrogen or $C_1$-$C_4$-alkyl or $C_1$-$C_4$-alkoxy and
one of the substituents R7 and R9 denotes $C_1$-$C_4$-alkoxy and the other denotes hydrogen or $C_1$-$C_4$-alkyl or $C_1$-$C_4$-alkoxy, and
R10 denotes hydrogen,
and hydrogen atoms are present in the 4- and 7-positions of the benzimidazole.

Embodiment a of the compounds which are to be singled out relates to those compounds of the formula I to be singled out in which R6 denotes hydrogen and R10 denotes hydrogen.

Embodiment b of the compounds which are to be singled out relates to those compounds of the formula I to be singled out in which R6 denotes $C_1$-$C_4$-alkyl and R10 denotes hydrogen.

Preferred compounds according to the invention are those in which

R1 denotes hydrogen, methyl or ethyl,
R2 denotes hydrogen, chlorine, fluorine, methyl, ethyl, methoxy or ethoxy,
R3 denotes hydrogen, methyl, ethyl, methoxy, ethoxy, 1,1,2,2-tetrafluoroethoxy, trifluoromethoxy, 2,2,2-trifluoroethoxy, difluoromethoxy or 2-chloro-1,1,2-trifluoroethoxy or, together with R4, denotes difluoromethylenedioxy, 1,1,2-trifluoroethylenedioxy or 1-chloro-1,2,2-trifluoroethylenedioxy,
R4 denotes 1,1,2,2-tetrafluoroethoxy, trifluoromethoxy, 2,2,2-trifluoroethoxy, difluoromethoxy or 2-chloro-1,1,2-trifluoroethoxy or, together with R3, denotes difluoromethylenedioxy, 1,1,2-trifluoroethylenedioxy or 1-chloro-1,2,2-trifluoroethylenedioxy,
R5 denotes hydrogen,
R6 denotes hydrogen, methyl or ethyl,
R7 denotes hydrogen, methyl, ethyl, methoxy or ethoxy,
R8 denotes hydrogen, methyl, ethyl, methoxy, ethoxy or allyloxy, R9 denotes hydrogen, methyl, ethyl, methoxy or ethoxy,
R10 denotes hydrogen, methyl or ethyl and
n represents the numbers 0 or 1,
and the salts of these compounds, with the proviso that a substituent R1, R2 or R3 in the 5- or 6-position in the benzimidazole cannot have the meanings of
hydrogen, chlorine, fluorine, methyl, ethyl, methoxy, ethoxy, 1,1,2,2-tetrafluoroethoxy, trifluoromethoxy, 2,2,2-trifluoroethoxy or difluoromethoxy or, together with R4—if this is in the 6- or 5-position—of difluoromethylenedioxy, 1,1,2-trifluoromethylenedioxy or 1-chloro-1,2,2-trifluoroethylenedioxy, if
R4 is in the 6- or 5-position and denotes 1,1,2,2-tetrafluoroethoxy, trifluoromethoxy, 2,2,2-trifluoroethoxy or difluoromethoxy or, together with R3—if this is in the 5- or 6-position—denotes difluoromethylenedioxy, 1,1,2-trifluoroethylenedioxy or 1-chloro-1,2,2-trifluoroethylenedioxy and
R5 denotes hydrogen and
R6 denotes hydrogen and
R7 denotes hydrogen or methyl or ethyl or methoxy or ethoxy and
R8 denotes hydrogen or methyl or methoxy or ethoxy and
R9 denotes hydrogen or methyl or ethyl or methoxy or ethoxy and
R10 denotes hydrogen
and hydrogen atoms are present in the 4- and 7-positions of the benzimidazole.

One aspect of the preferred compounds according to the invention are those of the formula in which
R1 denotes hydrogen, methyl or ethyl,
R2 denotes hydrogen, chlorine, fluorine, methyl, ethyl, methoxy or ethoxy,
R3 denotes hydrogen, methyl, ethyl, ethoxy, ethoxy, 1,1,2,2-tetrafluoroethoxy, trifluoromethoxy, 2,2,2-trifluoroethoxy, difluoromethoxy or 2-chloro-1,1,2-trifluoroethoxy or, together with R4, denotes difluoromethylenedioxy, 1,1,2-trifluoroethylenedioxy or 1-chloro-1,2,2-trifluoroethylenedioxy,
R4 denotes 1,1,2,2-tetrafluoroethoxy, trifluoromethoxy, 2,2,2-trifluoroethoxy, difluoromethoxy or 2-chloro-1,1,2-trifluoroethoxy or, together with R3, denotes difluoromethylenedioxy, 1,1,2-trifluoroethylenedioxy or 1-chloro-1,2,2-trifluoroethylenedioxy,
R5 denotes hydrogen,
R6 denotes hydrogen, methyl or ethyl,
R7 denotes hydrogen, methyl or ethyl,
R8 denotes hydrogen, methyl, ethyl, methoxy, ethoxy or allyloxy,
R9 denotes hydrogen, methyl or ethyl,
R10 denotes hydrogen, methyl or ethyl and
n represents the numbers 0 or 1,
and the salts of these compounds, with the proviso that a substituent R1, R2 or R3 in the 5- or 6-position in the benzimidazole cannot have the meanings of
hydrogen, chlorine, fluorine, methyl, ethyl, methoxy, ethoxy, 1,1,2,2-tetrafluoroethoxy, trifluoromethoxy, 2,2,2-trifluoroethoxy or difluoromethoxy or, together with R4—if this is in the 6- of 5-position—of difluoromethylenedioxy, 1,1,2-trifluoromethylenedioxy or 1-chloro-1,2,2-trifluoroethylenedioxy, if
R4 is in the 6- or 5-position and denotes 1,1,2,2-tetrafluoroethoxy, trifluoromethoxy, 2,2,2-trifluoroethoxy or difluoromethoxy or, together with R3—if this is in the 5- or 6-position—denotes difluoroethylenedioxy, 1,1,2-trifluoroethylenedioxy or 1-chloro-1,2,2-trifluoroethylenedioxy and
R5 denotes hydrogen and
R6 denotes hydrogen and
R7 denotes hydrogen or methyl or ethyl and
R8 denotes hydrogen or methyl or ethyl or methoxy or ethoxy and
R9 denotes hydrogen or methyl or ethyl and
R10 denotes hydrogen
and hydrogen atoms are present in the 4- and 7-positions of the benzimidazole.

A further aspect of the preferred compounds according to the invention are those of the formula in which
R1 denotes hydrogen, methyl or ethyl,
R2 denotes hydrogen, chlorine, fluorine, methyl, ethyl, methoxy or ethoxy,
R3 denotes hydrogen, methyl, ethyl, methoxy, ethoxy, 1,1,2,2-tetrafluoroethoxy, trifluoromethoxy, 2,2,2-trifluoroethoxy, difluoromethoxy or 2-chloro-1,1,2-trifluoroethoxy or, together with R4, denotes difluoromethylenedioxy, 1,1,2-trifluoroethylenedioxy or 1-chloro-1,2,2-trifluoroethylenedioxy,
R4 denotes 1,1,2,2-tetrafluoroethoxy, trifluoromethoxy, 2,2,2-trifluoroethoxy, difluoromethoxy or 2-chloro-1,1,2-trifluoroethoxy or, together with R3, denotes difluoromethylenedioxy, 1,1,2-trifluoroethylenedioxy or 1-chloro-1,2,2-trifluoroethylenedioxy,
R5 denotes hydrogen,
R6 denotes hydrogen, methyl or ethyl,
R8 denotes hydrogen, methyl, ethyl, methoxy, ethoxy or allyloxy,
one of the substituents R7 and R9 denotes methoxy or ethoxy and the other denotes hydrogen, methyl, ethyl, methoxy or ethoxy,
R10 denotes hydrogen and
n represents the numbers 0 or 1, and
the salts of these compounds with the proviso that a substituent R1, R2 or R3 in the 5- or 6-position in the benzimidazole cannot have the meanings of
hydrogen, chlorine, fluorine, methyl, ethyl, methoxy, ethoxy, 1,1,2,2-tetrafluoroethoxy, trifluoromethoxy, 2,2,2-trifluoroethoxy or difluoromethoxy or, together with R4—if this is in the 6- or 5-position—of difluoromethylenedioxy, 1,1,2-trifluoroethylenedioxy or 1-chloro-1,2,2-trifluoroethylenedioxy, if
R4 is in the 6- or 5-position and denotes 1,1,2,2-tetrafluoroethoxy, trifluoromethoxy, 2,2,2-trifluoroethoxy or difluoromethoxy or, together with R3—if this is in the 5- or 6-position—denotes difluoromethylenedioxy, 1,1,2-trifluoroethylenedioxy or 1-chloro-1,2,2-trifluoroethylenedioxy and
R5 denotes hydrogen and
R6 denotes hydrogen and
R8 denotes hydrogen or methyl or ethyl or methoxy or ethoxy and
one of the substituents R7 and R9 denotes methoxy or ethoxy and the other denotes hydrogen, methyl, ethyl, methoxy or ethoxy and
R10 denotes hydrogen,
and hydrogen atoms are present in the 4- and 7-positions of the benzimidazole.

Embodiment a of the preferred compounds relates to those preferred compounds of the formula I in which R6 denotes hydrogen and R10 denotes hydrogen.

Embodiment b of the preferred compounds relates to those preferred compounds of the formula I in which R6 denotes methyl or ethyl and R10 denotes hydrogen.

Particularly preferred compounds according to the invention are those of the formula I in which
R1 denotes hydrogen,
R2 denotes hydrogen, methyl or methoxy,
R3 denotes hydrogen, methyl, methoxy, 1,1,2,2-tetrafluoroethoxy, difluoromethoxy or 2-chloro-1,1,2-trifluoroethoxy or, together with R4, denotes difluoromethylenedioxy,
R4 denotes 1,1,2,2-tetrafluoroethoxy, difluoromethoxy or 2-chloro-1,1,2-trifluoroethoxy or, together with R3, denotes difluoromethylenedioxy,
R5 denotes hydrogen,
R6 denotes hydrogen or methyl,
R7 denotes hydrogen, methyl or methoxy,
R8 denotes methoxy,
R9 denotes hydrogen,
R10 denotes hydrogen and
n represents the numbers 0 or 1, and
the salts of these compounds, with the proviso that a substituent R1, R2 or R3 in the 5- or 6-position in the benzimidazole cannot have the meanings of
hydrogen, methyl methoxy, 1,1,2,2-tetrafluoroethoxy or difluoromethoxy or, together with R4—if this is in the 6- or 5-position—of difluoromethylenedioxy, if
R4 is in the 6- or 5-position and denotes 1,1,2,2-tetrafluoroethoxy or difluoromethoxy or, together with R3—if this is in the 5- or 6-position—denotes difluoromethylenedioxy and
R5 denotes hydrogen and
R6 denotes hydrogen and
R7 denotes hydrogen, methyl or methoxy and
R8 denotes methoxy and
R9 denotes hydrogen and
R10 denotes hydrogen,
and hydrogen atoms are present in the 4- and 7-positions of the benzimidazole.

One aspect of the particularly preferred compounds according to the invention are those of the formula I in which
R1 denotes hydrogen,
R2 denotes hydrogen, methyl or methoxy,
R3 denotes hydrogen, methyl, methoxy, 1,1,2,2-tetrafluoroethoxy, difluoromethoxy or 2-chloro-1,1,2-trifluoroethoxy, or, together with R4, denotes difluoromethylenedioxy,
R4 denotes 1,1,2,2-tetrafluoroethoxy, difluoromethoxy or 2-chloro-1,1,2-trifluoroethoxy or, together with R3, denotes difluoromethylenedioxy,
R5 denotes hydrogen,
R6 denotes hydrogen or methyl,
R7 denotes hydrogen or methyl,
R8 denotes methoxy,
R9 denotes hydrogen,
R10 denotes hydrogen and
n represents the numbers 0 or 1, and
the salts of these compounds, with the proviso that a substituent R1, R2 or R3 in the 5- or 6-position in the benzimidazole cannot have the meanings of
hydrogen, methyl, methoxy, 1,1,2,2-tetrafluoroethoxy or difluoromethoxy or, together with R4—if this is in the 6- or 5-position—of difluoromethylenedioxy, if
R4 is in the 6- or 5-position and denotes 1,1,2,2-tetrafluoroethoxy or difluoromethoxy or, together with R3—if this is in the 5- or 6-position—denotes difluoromethylenedioxy and
R5 denotes hydrogen and
R6 denotes hydrogen and
R7 denotes hydrogen or methyl and
R8 denotes methoxy and
R9 denotes hydrogen and
R10 denotes hydrogen
and hydrogen atoms are present in the 4- and 7-positions of the benzimidazole.

A further aspect of the particularly preferred compounds according to the invention are those of the formula I in which
R1 denotes hydrogen,
R2 denotes hydrogen, methyl or methoxy,
R3 denotes hydrogen, methyl, methoxy, 1,1,2,2-tetrafluoroethoxy, difluoromethoxy or 2-chloro-1,1,2-trifluoroethoxy or, together with R4, denotes difluoromethylenedioxy,
R4 denotes 1,1,2,2-tetrafluoroethoxy, difluoromethoxy or 2-chloro-1,1,2-trifluoroethoxy or, together with R3, denotes difluoromethylenedioxy,
R5 denotes hydrogen,
R6 denotes hydrogen or methyl,
R7 denotes methoxy,
R8 denotes methoxy,
R9 denotes hydrogen,
R10 denotes hydrogen and
n represents the numbers 0 or 1, and
the salts of these compounds, with the proviso that a substituent R1, R2 or R3 in the 5- or 6-position in the benzimidazole cannot have the meanings of
hydrogen, methyl, methoxy, 1,1,2,2-tetrafluoroethoxy or difluoromethoxy or, together with R4—if this is in the 6- or 5-position—of difluoromethylenedioxy, if
R4 is in the 6- or 5-position and denotes 1,1,2,2-tetrafluoroethoxy or difluoromethoxy or, together with R3—if this is in the 5- or 6-position—denotes difluoromethylenedioxy and
R5 denotes hydrogen and
R6 denotes hydrogen and
R7 denotes methoxy and
R8 denotes methoxy and
R9 denotes hydrogen and
R10 denotes hydrogen and
hydrogen atoms are present in the 4- and 7-positions of the benzimidazole.

In the preferred and particularly preferred compounds according to the invention or in their embodiments a and b the substituents R3 and R4 are especially in the 5- and 6-positions of the benzimidazole.

In the compounds of the formula I, wherein R5 denotes hydrogen, the 4-position and the 7-position in the benzimidazole, and the 5-position and the 6-position, are indentical due to the tautomery in the imidazole ring.

Examples which may be mentioned of compounds according to the invention are:
5-difluoromethoxy-2-[(4-methoxy-3-methyl-2-pyridyl)-methylthio]-4,6-dimethyl-1H-benzimidazole,
5-difluoromethoxy-2-[(4-methoxy-3,5-dimethyl-2-pyridyl)methylthio]-4,6-dimethyl-1H-benzimidazole,
5-difluoromethoxy-2-{[4-(2-methoxyethoxy)-3-methyl-2-pyridyl]methylthio}-4,6-dimethyl-1H-benzimidazole,
5-difluoromethoxy-4,6-dimethyl-2-[(4-methyl-2-pyridyl)methylthio]-1H-benzimidazole,
5-difluoromethoxy-4,6-dimethyl-2-[(3-methyl-2-pyridyl)methylthio]-1H-benzimidazole,
5-difluoromethoxy-4,6-dimethyl-2-[(5-methyl-2-pyridyl)methylthio]-1H-benzimidazole,
2-[(4-allyloxy-3-methyl-2-pyridyl)methylthio]-5-difluoromethoxy-4,6-dimethyl-1H-benzimidazole, 5-difluoromethoxy-4,6-dimethoxy-2-[(4-methoxy-3-methyl-2-pyridyl)methylthio]-1H-benzimidazole,
5-difluoromethoxy-4,6-dimethoxy-2-[(4-methoxy-3,5-dimethyl-2-pyridyl)methylthio]-1H-benzimidazole,
5-difluoromethoxy-4,6-dimethoxy-2-[(3,5-dimethyl-2-pyridyl)methylthio]-1H-benzimidazole,
2-[(4-allyloxy-3-methyl-2-pyridyl)methylthio]-5-difluoromethoxy-4,6-dimethoxy-1H-benzimidazole,
4-difluoromethoxy-2-[(4-methoxy-2-pyridyl)methylthio]-6-methyl-1H-benzimidazole,
4-difluoromethoxy-2-[(4-methoxy-3-methyl-2-pyridyl)methylthio]-6-methyl-1H-benzimidazole,
4-difluoromethoxy-2-[(4-methoxy-3-methyl-2-pyridyl)methylthio]-7-methyl-1H-benzimidazole,
5-difluoromethoxy-2-[(4-methoxy-2-pyridyl)methylthio]-4,6,7-trimethyl-1H-benzimidazole,
2-[(4-allyloxy-3-methyl-2-pyridyl)methylthio]-5-difluoromethoxy-6-methyl-1H-benzimidazole,
5-difluoromethoxy-2-[(4-methoxy-2-pyridyl)methylthio]-6,7-dimethyl-1H-benzimidazole,
5-difluoromethoxy-2-[(4-methoxy-3-methyl-2-pyridyl)methylthio]-6,7-dimethyl-1H-benzimidazole,
5-difluoromethoxy-2-[(4-methoxy-3-methyl-2-pyridyl)methylthio]-6-(2-methoxyethoxy)-1H-benzimidazole,
5-(2-chloro-1,1,2-trifluoroethoxy)-2-[(4-methoxy-2-pyridyl)methylthio]-4,6-dimethyl-1H-benzimidazole,
5-(2-chloro-1,1,2-trifluoroethoxy)-2-[(4-methoxy-3-methyl-2-pyridyl)-methylthio]-4,6-dimethyl-1H-benzimidazole,
2-[(4-allyloxy-3-methyl-2-pyridyl)methylthio]-5-(2-chloro-1,1,2-trifluoroethoxy)-1H-benzimidazole,
5-(2-chloro-1,1,2-trifluoroethoxy)-2-[(4-methoxy-2-pyridyl)methylthio]-1H-benzimidazole,
5-(2-chloro-1,1,2-trifluoroethoxy)-2-[(4-methoxy-3-methyl-2-pyridyl)-methylthio]-1H-benzimidazole,
5-(2-chloro-1,1,2-trifluoroethoxy)-2-[(4-methoxy-5-methyl-2-pyridyl)methylthio]-1H-benzimidazole,
5-(2-chloro-1,1,2-trifluoroethoxy)-6-methoxy-2-[(4-methoxy-2-pyridyl)methylthio]-1H-benzimidazole,
2-[(4-allyloxy-3-methyl-2-pyridyl)methylthio]-5-methoxy-6-(1,1,2,2-tetrafluoroethoxy)-1H-benzimidazole,
2-[(4-allyloxy-3-methyl-2-pyridyl)methylthio]-5-(1,1,2,2-tetrafluoroethoxy)-1H-benzimidazole,
2-[(4-allyloxy-2-pyridyl)methylthio]-5-(1,1,2,2-tetrafluoroethoxy)-1H-benzimidazole,
2-[(4-allyloxy-3-methyl-2-pyridyl)methylthio]-5-difluoromethoxy-6-methoxy-1H-benzimidazole,
2-[(4-allyloxy-3-methyl-2-pyridyl)methylthio]-5-difluoromethoxy-1H-benzimidazole,
2-[(4-allyloxy-3,5-dimethyl-2-pyridyl)methylthio]-5-trifluoromethoxy-1H-benzimidazole,
6-[(4-allyloxy-2-pyridyl)methylthio]-2,2-difluoro-5H-[1.3]-dioxolo-[4.5-f]-benzimidazole,
6-[(4-allyloxy-3-methyl-2-pyridyl)methylthio]-2,2-difluoro-5H-[1.3]-dioxolo[4.5-f]benzimidazole,
6-[(4-allyloxy-3,5-dimethyl-2-pyridyl)methylthio]-2,2-difluoro-5H-[1.3]-dioxolo[4.5-f]benzimidazole,
2,2-difluoro-6-{[4-(2-methoxyethoxy)-3-methyl-2-pyridyl]-methylthio}-5H-[1.3]-dioxolo[4.5-f]benzimidazole,
2-[(4-allyloxy-2-pyridyl)methylthio]-6,6,7-trifluoro-6,7-dihydro-1H-[1.4]-dioxino[2.3-f]benzimidazole,
2,2-difluoro-6-[(4-methoxy-2-pyridyl)methylthio]-4-methyl-5H-[1.3]-dioxolo[4.5-f]benzimidazole,
2,2-difluoro-6-[(4-methoxy-3-methyl-2-pyridyl)methylthio]-4-methyl-5H-[1.3]-dioxolo[4.5-f]benzimidazole, 2,2-difluoro-4-methoxy-6-[(4-methoxy-3-methyl-2-pyridyl)methylthio]-5H-[1.3]-dioxolo[4.5-f]benzimidazole,
4-difluoromethoxy-7-methoxy-2-[(4-methoxy-3-methyl-2-pyridyl)methylthio]-5-methyl-1H-benzimidazole,
5-difluoromethoxy-2-[(4-methoxy-3-methyl-2-pyridyl)-methylsulphinyl]-4,6-dimethyl-1H-benzimidazole,
5-difluoromethoxy-2-[(4-methoxy-3,5-dimethyl-2-pyridyl)methylsulphinyl]-4,6-dimethyl-1H-benzimidazole,
5-difluoromethoxy-2-{[4-(2-methoxyethoxy)-3-methyl-2-pyridyl]methylsulphinyl}-4,6-dimethyl-1H-benzimidazole,
5-difluoromethoxy-4,6-dimethyl-2-[(4-methyl-2-pyridyl)methylsulphinyl]-1H-benzimidazole,
5-difluoromethoxy-4,6-dimethyl-2-[(3-methyl-2-pyridyl)methylsulphinyl]-1H-benzimidazole,
5-difluoromethoxy-4,6-dimethyl-2-[(5-methyl-2-pyridyl)methylsulphinyl]-1H-benzimidazole,
2-[(4-allyloxy-3-methyl-2-pyridyl)methylsulphinyl]-5-difluoromethoxy-4,6-dimethyl-1H-benzimidazole,
5-difluoromethoxy-4,6-dimethoxy-2-[(4-methoxy-3-methyl-2-pyridyl)methylsulphinyl]-1H-benzimidazole,
5-difluoromethoxy-4,6-dimethoxy-2-[(4-methoxy-3,5-dimethyl-2-pyridyl)methylsulphinyl]-1H-benzimidazole,
5-difluoromethoxy-4,6-dimethoxy-2-[(3,5-dimethyl-2-pyridyl)methylsulphinyl]-1H-benzimidazole,
2-[(4-allyloxy-3-methyl-2-pyridyl)methylsulphinyl]-5-difluoromethoxy-4,6-dimethoxy-1H-benzimidazole,
4-difluoromethoxy-2-[4-methoxy-2-pyridyl)methylsulphinyl]-6-methyl-1H-benzimidazole,
4-difluoromethoxy-2-[(4-methoxy-3-methyl-2-pyridyl)methylsulphinyl]-6-methyl-1H-benzimidazole,
4-difluoromethoxy-2-[(4-methoxy-3-methyl-2-pyridyl)methylsulphinyl]-7-methyl-1H-benzimidazole,
5-difluoromethoxy-2-[(4-methoxy-2-pyridyl)methylsulphinyl]-4,6,7-trimethyl-1H-benzimidazole,
2-[(4-allyloxy-3-methyl-2-pyridyl)methylsulphinyl]-5-difluoromethoxy-6-methyl-1H-benzimidazole,
5-difluoromethoxy-2-[(4-methoxy-2-pyridyl)methylsulphinyl]-6,7-dimethyl-1H-benzimidazole,
5-difluoromethoxy-2-[(4-methoxy-3-methyl-2-pyridyl)methylsulphinyl]-6,7-dimethyl-1H-benzimidazole,
5-difluoromethoxy-2-[(4-methoxy-3-methyl-2-pyridyl)methylsulphinyl]-6-(2-methoxyethoxy)-1H-benzimidazole,
5-(2-chloro-1,1,2-trifluoroethoxy)-2-[(4-methoxy-2-pyridyl)methylsulphinyl]-4,6-dimethyl-1H-benzimidazole,
5-(2-chloro-1,1,2-trifluoroethoxy)-2-[(4-methoxy-3-methyl-2-pyridyl)methylsulphinyl]-4,6-dimethyl-1H-benzimidazole,
2-[(4-allyloxy-3-methyl-2-pyridyl)methylsulphinyl]-5-(2-chloro-1,1,2-trifluoroethoxy)-1H-benzimidazole,
5-(2-chloro-1,1,2-trifluoroethoxy)-2-[(4-methoxy-2-pyridyl)methylsulphinyl]-1H-benzimidazole,
5-(2-chloro-1,1,2-trifluoroethoxy)-2-[(4-methoxy-3-methyl-2-pyridyl)methylsulphinyl]-1H-benzimidazole,
5-(2-chloro-1,1,2-trifluoroethoxy)-2-[(4-methoxy-5-methyl-2-pyridyl)methylsulphinyl]-1H-benzimidazole,
5-(2-chloro-1,1,2-trifluoroethoxy)-6-methoxy-2-[(4-methoxy-2-pyridyl)methylsulphinyl]-1H-benzimidazole, 2-[(4-allyloxy-3-methyl-2-pyridyl)methylsulphinyl]-5-methoxy-6-(1,1,2,2-tetrafluoroethoxy)-1H-benzimidazole,
2-[(4-allyloxy-3-methyl-2-pyridyl)methylsulphinyl]-5-(1,1,2,2-tetrafluoroethoxy)-1H-benzimidazole,
2-[(4-allyloxy-2-pyridyl)methylsulphinyl]-5-(1,1,2,2-tetrafluoroethoxy)-1H-benzimidazole,
2-[(4-allyloxy-3-methyl-2-pyridyl)methylsulphinyl]-5-difluoromethoxy-6-methoxy-1H-benzimidazole,
2-[(4-allyloxy-3-methyl-2-pyridyl)methylsulphinyl]-5-difluoromethoxy-1H-benzimidazole,
2-[(4-allyloxy-3,5-dimethyl-2-pyridyl)methylsulphinyl]-5-trifluoromethoxy-1H-benzimidazole,
6-[(4-allyloxy-2-pyridyl)methylsulphinyl]-2,2-difluoro-5H-[1.3]-dioxolo[4.5-f]benzimidazole,
6-[(4-allyloxy-3-methyl-2-pyridyl)methylsulphinyl]-2,2-difluoro-5H-[1.3]-dioxolo[4.5-f]benzimidazole,
6-[(4-allyloxy-3,5-dimethyl-2-pyridyl)methylsulphinyl]-2,2-difluoro-5H-[1.3]-dioxolo[4.5-f]benzimidazole,
2,2-difluoro-6-{[4-(2-methoxyethoxy)-3-methyl-2-pyridyl]methylsulphinyl}-5H-[1.3]-dioxolo[4.5-f]benzimidazole,
2-[(4-allyloxy-2-pyridyl)methylsulphinyl]-6,6,7-trifluoro-6,7-dihydro-1H-[1.4]-dioxino[2.3-f]benzimidazole,
2,2-difluoro-6-[(4-methoxy-2-pyridyl)methylsulphinyl]-4-methyl-5H-[1.3]-dioxolo[4.5-f]benzimidazole,
2,2-difluoro-6-[(4-methoxy-3-methyl-2-pyridyl)methylsulphinyl]-4-methyl-5H-[1.3]-dioxolo[4.5-f]benzimidazole,
2,2-difluoro-4-methoxy-6-[(4-methoxy-3-methyl-2-pyridyl)methylsulphinyl]-5H-[1.3]-dioxolo[4.5-f]benzimidazole and
4-difluoromethoxy-7-methoxy-2-[(4-methoxy-3-methyl-2-pyridyl)methylsulphinyl]-5-methyl-1H-benzimidazole
and their salts.

The invention also relates to a process for the preparation of the compounds of the formula I, wherein R1, R2, R3, R4, R5, R6, R7, R8, R9, R10 and n have the meanings given above, and of their salts.

The process is characterized in that (a) mercaptobenzimidazoles of the formula II are reacted with picoline derivatives III,

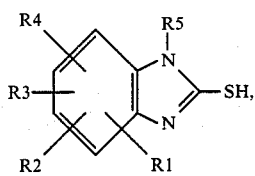

(II)

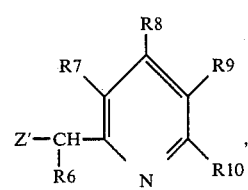

(III)

or (b) benzimidazoles of the formula IV are reacted with mercaptopicolines V,

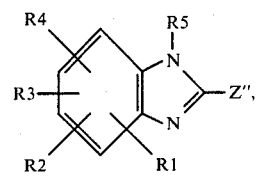

(IV)

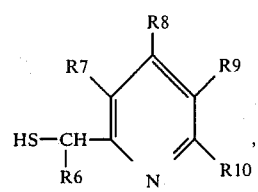

(V)

or (c) o-phenylenediamines of the formula VI are reacted with formic acid derivatives VII

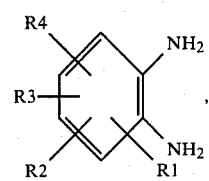

(VI)

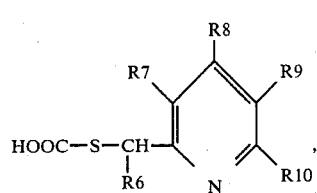

(VII)

and (if compounds of the formula I with n=1 are the desired end products) the 2-benzimidazolyl 2-pyridylmethyl sulphides of the formula VIII (=compounds of the formula I with n=0).

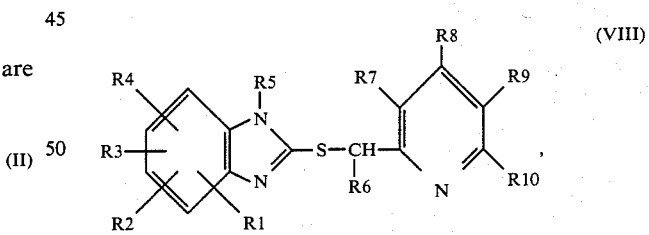

(VIII)

obtained according to (a), (b) or (c) are then oxidised and/or or, if desired, converted into the salts, or that (d) benzimidazoles of the formula IX are reacted with pyridine derivatives X

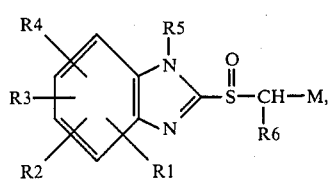

(IX)

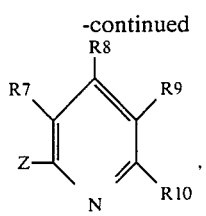

or (e) sulphinyl derivatives of the formula XI are reacted with 2-picoline derivatives XII

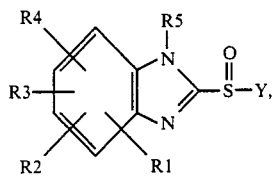

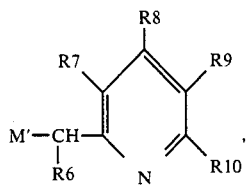

and, if desired, are subsequently converted into the salts, or (f)—if compounds of the formula I, wherein R5 represents a group which can readily be eliminated under physiological conditions, are the process products to be prepared—compounds of the formula I wherein R5 denotes hydrogen are reacted with compounds of the formula R5'—Y' (XIII), wherein R5' is the desired group which can be readily eliminated under physiological conditions or, together with Y', is its precursor, and, if desired, the products are then converted into the salts, or (g)—if compounds of the formula I, wherein R5 denotes hydrogen, are the process products to be prepared—compounds of the formula I, wherein R5 represents a group which can be readily eliminated under physiological conditions, are solvolysed, and the products obtained are, if desired, converted into the salts, or (h)—if compounds of the formula I, wherein R6 notes $C_1$-$C_6$-alkyl, are the process products to be prepared—compounds of the formula I, wherein R6 denotes hydrogen, are alkylated with compounds of the formula R6—Y" (XIV), wherein R6 denotes $C_1$-$C_6$-alkyl, and, if desired, are then converted into the salts, Y, Y", Z, Z' and Z" representing suitable leaving groups, Y' representing a leaving group or reactive group, M representing an alkali metal atom (Li, Na or K), M' representing the equivalent of a metal atom and R1, R2, R3, R4, R5, R6, R7, R8, R9, R10 and n (unless otherwise defined) having the meanings given above.

In the reactions listed above, the compounds II–XIV can be employed as such, or if appropriate, in the form of their salts.

The preparation processes (a), (b) and (c) lead to the sulphides according to the invention, the oxidation of the compounds VIII and the processes (d) and (e) furnish the sulphoxides according to the invention, and the processes (f), (g) and (h) lead to both product classes.

Based on their specialist knowledge, those skilled in the art are familiar with the leaving groups Y, Y', Y", Z, Z' or Z" which are suitable. A suitable leaving group Y is, for example, a group which, together with the sulphinyl group, to which it is bonded, forms a reactive sulphinic acid derivative. Alkoxy, dialkylamino or alkylmercapto groups may be mentioned as examples of a suitable leaving group Y. A suitable leaving or reactive group Y' is a group which is capable of reacting with a secondary amino group, with elimination of HY' or with addition. In the case of compounds of the formula XIII, in which R5' represents in particular a substituted carbonyl group, Y' is, for example, a leaving group which, together with the carbonyl group to which it is bonded, forms a reactive carboxylic acid derivative, for example an acid halide. According to the invention, the general formula R5'—Y' (XIII) comprises also those compounds (precursors of the group R5 which can be readily eliminated under physiological conditions) in which Y' represents a reactive group (for example isonitriles) which, in the reaction with the secondary amino group, do not undergo a condensation with elimination of HY' but an addition with formation of the desired group R5 which can be eliminated.

The leaving group Y" is a group with which an expert in alkylation reactions is familiar and which is eliminated in the alkylation—for example with dialkyl sulphate, alkyl fluorosulphonate or alkyl iodide.

Halogen atoms, in particular chlorine atoms, or hydroxyl groups activated by esterification (for example with p-toluenesulphonic acid) may be mentioned as examples of suitable leaving groups Z, Z' or Z".

The equivalent of a metal atom M' is, for example, an alkali metal salt (Li, Na or K) or an alkaline earth metal atom (for example Mg) which is substituted by a halogen atom (for example Br, Grignard reagent), or any other substituted or unsubstituted metal atom, of which it is known that it reacts like the abovementioned metals in substitution reactions of metal-organic compounds.

The reaction of II with III is carried out in a manner known per se in suitable, preferably polar protic or aprotic solvents (such as methanol, isopropanol, dimethyl sulphoxide, acetone, dimethylformamide or acetonitrile) with addition or with exclusion of water. It is carried out, for example, in the presence of a proton acceptor. As the latter, alkali metal hydroxides are suitable, such as sodium hydroxide, alkali metal carbonates, such as potassium carbonate, or tertiary amines, such as pyridine, triethylamine or ethyldiisopropylamine. Alternatively, the reaction can also be carried out without a proton acceptor, in which case—depending on the nature of the starting compounds—the acid addition salts can, if appropriate, initially be separated off in a particularly pure form. The reaction temperature can be between 0° and 150° C., temperatures between 20° and 80° C. being preferred in the presence of proton acceptors, and temperatures between 60° and 120° C.—in particular the boiling point of the solvent used—being preferred without proton acceptors. The reaction times are between 0.5 and 12 hours.

In the reaction of IV with V, which takes place in a manner known per se, similar reaction conditions as in the reaction of II with III are applied.

The reaction of VI with VII is preferably carried out in polar solvents, which may contain water, in the presence of a strong acid, for example hydrochloric acid, in particular at the boiling point of the solvent used.

The oxidation of the sulphides VIII takes place in a manner known per se and under the conditions such as are familiar to an expert in the oxidation of sulphides to sulphoxides (in this connection, see, for example, J. Drabowicz and M. Mikolajczyk, Organic preparations and procedures int. 14(1-2), 45-89 (1982) or E. Block in S. Patai, The Chemistry of Functional Groups, Supplement E. Part 1, pages 539-608, John Wiley and Sons (Interscience Publication), 1980). The oxidising agents which can be used are all reagents customarily used for the oxidation of sulphides to sulphoxides, in particular peroxy acids, such as, for example, peroxyacetic acid, trifluoroperoxyacetic acid, 3,5-dinitroperoxybenzoic acid, peroxymaleic acid or preferably m-chloroperoxybenzoic acid.

The reaction temperature (depending on the reactivity of the oxidising agent and the degree of dilution) is between $-70°$ C. and the boiling point of the solvent used, but preferably between $-30°$ and $+20°$ C. The oxidation with halogens or with hypohalites (for example with aqueous sodium hypochlorite solution) has also proved advantageous and is expediently carried out at temperatures between $0°$ and $30°$ C. The reaction is advantageously carried out in inert solvents, for example aromatic or chlorinated hydrocarbons, such as benzene, toluene, dichloromethane or chloroform, preferably in esters or ethers, such as ethyl acetate, isopropyl acetate or dioxane.

The reaction of IX with X is preferably carried out in inert solvents, such as are also customarily used for the reaction of enolate ions with alkylating agents. Aromatic solvents such as benzene or toluene may be mentioned as examples. The reaction temperature is (depending on the nature of the alkali metal atom M and the leaving group Z) as a rule between $0°$ and $120°$ C., the boiling point of the solvent used being preferred. For example [when M represents Li (lithium) and Z represents Cl (chlorine) and the reaction is carried out in benzene] the boiling point of benzene ($80°$ C.) is preferred.

The compounds XI are reacted with the compounds XII in a manner known per se, such as is familiar to an expert in the reaction of metal-organic compounds.

The reaction according to process variant (f) takes place in a manner known to an expert in suitable solvents such as tetrahydrofuran or acetonitrile, if appropriate with the addition of a base (if Y' represents a leaving group) or without base addition (if Y' represents a reactive group). In the case of an unsymmetrical distribution of the substituents R1, R2, R3 and R4, this reaction gives mixtures of isomers, which must be separated by suitable separation processes (for example chromatography).

The solvolysis according to process variant (g) takes place in a manner known to an expert, in suitable alkaline or acidic solution which contain water or release water, at room temperature or, if desired, with heating up to the boiling point of the solvent employed.

The alkylation according to process variant (h) takes place—if appropriate after preceding deprotonation—in suitable inert solvents in a manner familiar to an expert.

Depending on the nature of the starting compounds which, if appropriate, can also be employed in the form of their salts, and as a function of the reaction conditions, the compounds according to the invention are initially obtained either as such or in the form of their salts.

In other cases, the salts are obtained by dissolving the free compounds in a suitable solvent, for example in a chlorinated hydrocarbon, such as methylene chloride or chloroform, a low-molecular aliphatic alcohol (ethanol, isopropanol), an ether (diisopropyl ether), a ketone (acetone) or water, which contains the desired acid or base or to which the desired acid or base—if appropriate in the precisely calculated stoichiometric amount—is subsequently added.

The salts are obtained by filtration, reprecipitation, precipitation or by evaporation of the solvent.

The salts obtained can be converted into the free compounds by alkalising or acidifying, for example, with aqueous sodium bicarbonate or with dilute hydrochloric acid, and the free compounds can in turn be converted into the salts. The compounds can be purified in this way, or pharmacologically unacceptable salts can be converted into pharmacologically acceptable salts.

The sulphoxides according to the invention are optically active compounds. Depending on the nature of the substituents R1 to R10, yet further chirality centres can be present in the molecule (for example if R6 is not hydrogen). The invention therefore comprises the enantiomers and diastereomers as well as their mixtures and racemates. The enantiomers can be resolved in a manner known per se (for example by preparation and separation of corresponding diastereoisomeric compounds). However, the enantiomers can also be prepared by asymmetrical synthesis, for example by reaction of optically active pure compounds XI or diastereoisomerically pure compounds XI with compounds XII [in this connection, see K. K. Andersen, Tetrahedron Lett., 93 (1962)].

The compounds according to the invention are preferably synthesised by reaction of II with III and, if appropriate, subsequent oxidation of the resulting sulphide VIII.

The compounds II, IV, VI, IX and XI are new and are likewise subjects of the invention. They can be obtained by known methods in an analogous manner, starting from precursors which are known or obtainable in a known manner [see, for example, German Offenlegungsschrift No. 2,848,531; J. Org. Chem. 44, 2907-2910 (1979); J. Org. Chem. 29, 1-11 (1964); German Offenlegungsschrift No. 2,029,556; J. Fluorine Chem. 18, 281-91 (1981); Synthesis 1980, 727-8; Bull. Soc. Chim. France 4, 581-592 (1957); C.A. 60, 13352h (1964)].

Some of the compounds III, V, VII, X and XII are known or can be prepared analogously by known methods (see, for example, German Offenlegungsschrift No. 3,404,610), or they can—depending on the substituent pattern—be prepared for example, as follows:

1. Compounds III where R7 and R8=1-3C-alkoxy and R9=hydrogen or 1-3C-alkyl.

These compounds are prepared, for example, starting from 3-hydroxy- or 3-hydroxy-5-alkyl-pyridines which are known or can be prepared by a known route, by benzylation of the hydroxyl group (for example with potassium hydroxide and benzyl chloride in dimethyl sulphoxide), N-oxidation (for example with 30% strength hydrogen peroxide), nitration in the 4-position (for example with nitrating acid), replacement of the nitro group by the 1-3C-alkoxy group (for example by reaction with alkali metal alkoxide), reductive debenzylation and simultaneous N-deoxygenation (for example with hydrogen over palladium-on-charcoal in an acid medium), introduction of the hydroxymethyl group in the o-position relative to the pyridine nitrogen (for example by reaction with alkaline formalin solution), conversion of the 3-hydroxy group into a 1-3C-alkoxy group (for example by alkylation with 1-3C-alkyl iodide in a basic medium) and introduction of the leaving group Z' (for example by reaction with thionyl chloride). In a preferred alternative, the compounds are prepared starting from 3-hydroxy-2-alkyl- or 3-hydroxy-2,5-dialkyl-pyridines, which are known or can be prepared by a known route, by alkylation of the hydroxyl group (for example with potassium hydroxide and methyl iodide in dimethyl sulphoxide), N-oxidation (for example with 30% strength hydrogen peroxide), nitration in the 4-position (for example with nitric acid), replacement of the nitro group by the 1-3C-alkoxy group (for example by reaction with alkali metal alkoxide), conversion into the 2-acetoxymethylpyridine (for example with hot acetic anhydride), hydrolysis (for example with dilute sodium hydroxide solution) to the hydroxymethyl group and introduction of the leaving group Z' (for example by reaction with thionyl chloride).

2. Compounds III where R8 and R9=1-3C-alkoxy and R7=hydrogen.

These compounds are prepared, for example, starting from known 5-hydroxy-2-methylpyridines by alkylation of the hydroxyl group (for example with 1-3C-alkyl iodide and potassium hydroxide in dimethyl sulphoxide), N-oxidation (for example with 30% strength hydrogen peroxide), nitration in the 4-position (for example with nitrating acid), replacement of the nitro group by the 1-3C-alkoxy group (for example by reaction with alkali metal alkoxide), conversion into the 2-acetoxymethylpyridine (for example with hot acetic anhydride), hydrolysis (for example with dilute sodium hydroxide solution) to the 2-hydroxymethyl group and introduction of the leaving group Z' (for example by reaction with thionyl chloride).

3. Compounds III where R8 and R9=1-3C-alkoxy and R7=1-3C-alkyl.

These compounds are prepared, for example, starting from 2-methyl-3-alkyl-4-alkoxypyridines which are known or can be prepared by a known route (see, for example, European Patent A-0,080,602), by N-oxidation (for example with 30% strength hydrogen peroxide), controlled acetoxylation and subsequent hydrolysis in the 5-position (for example with acetic anhydride and subsequently sodium hydroxide solution), alkylation of the 5-hydroxy group (for example with 1-3C-alkyl iodide and sodium hydroxide solution in dimethyl sulphoxide), N-oxidation (for example with m-chloroperoxybenozic acid), conversion into the 2-acetoxymethylpyridine (for example with hot acetic anhydride), hydrolysis (for example with dilute sodium hydroxide solution) to the 2-hydroxymethyl group and introduction of the leaving group Z' (for example by reaction with thionyl chloride).

The specific reaction conditions (temperatures, reaction times, solvents and the like) in the synthesis routes outlined above for the preparation of the compounds III which are necessary are familiar to the expert on the basis of his expert knowledge. Precise preparation of individual representatives of the compounds III is described in the examples. Other representatives are prepared analogously.

Compounds of the formula III in which R6 has a meaning other than hdrogen are obtained, for example, from the corresponding pyridine-2-alkyl compounds by reaction with acetic anhydride, subsequent reaction with sodium hydroxide solution and conversion of the alcohol formed into the corresponding halogen compound (for example by means of thionyl chloride) in a manner known to those skilled in the art.

The compounds V, VII and XII are prepared, for example, starting from the compounds III by methods known to those skilled in the art. The compounds X are prepared in analogy to Z. Talik, Roczniki Chem. 35, 475 (1961).

The examples which follow illustrate the invention in more detail without restricting it. The compounds, listed by name in the examples, of the general formula I and the salts of these compounds are preferred subjects of the invention, m.p. means melting point, b.p. means boiling point, the abbreviation h is used for hour(s) and the abbreviation min. is used for minutes. "Ether" is to be understood as diethyl ether.

EXAMPLES

End Products

1.

5-Difluoromethoxy-2-[(4-methoxy-3-methyl-2-pyridyl)-methylsulphinyl]-4,6-dimethyl-1H-benzimidazole A solution of 0.47 g of 81% m-chloroperoxybenzoic acid in 40 ml of dichloromethane is added dropwise at −40° C. to a solution of 0.80 g of 5-difluoromethoxy-2-[(4-methoxy-3-methyl-2-pyridyl)methylthio]-4,6-dimethyl-1H-benzimidazole in 40 ml of dichloromethane. Stirring is continued for a further 2 h at −40° C., 0.31 ml of triethylamine is added at −20° C. and the mixture is extracted at 0° C. with potassium bicarbonate solution and water. The organic solution is dried and concentrated, and the product is allowed to crystallise from diisopropyl ether. This gives 0.6 g (73%) of the title compound of m.p. 182°–183° C. (decomposition).

Analogously, the following are obtained by oxidation with m-chloroperoxybenzoic acid:

5-difluoromethoxy-2-[(4-methoxy-2-pyridyl)methylsulphinyl]-4,6-dimethyl-1H-benzimidazole (m.p. 163°–164° C. with decomposition) from 5-difluoromethoxy-2-[(4-methoxy-2-pyridyl)methylthio]-4,6-dimethyl-1H-benzimidazole, 4-difluoromethoxy-5,6-dimethoxy-2-[(4-methoxy-3-methyl-2-pyridyl)methylsulphinyl]-1H-benzimidazole (m.p. 180°–181° C. with decomposition) from 4-difluoromethoxy-5,6-dimethoxy-2-[(4-methoxy-3-methyl-2-pyridyl)methylthio]-1H-benzimidazole, 4-difluoromethoxy-5,6-dimethoxy-2-[(4-methoxy-2-pyridyl)methylsulphinyl]-1H-benzimidazole (m.p. 154°–155° C. with decomposition) from 4-difluoromethoxy-5,6-dimethoxy-2-[(4-methoxy-2-pyridyl)methylthio]-1H-benzimidazole, 5-difluoromethoxy-6-methoxy-2-{[1-(4-methoxy-2-pyridyl)ethyl]sulphinyl}-1H-benzimidazole (m.p. 152°–153° C. with decomposition; from ethyl acetate) from 5-difluoromethoxy-6-methoxy-2-{[1-(4-methoxy-2-pyridyl)ethyl]thio}-1H-benzimidazole, 5-difluoromethoxy-2-{[1-(4-methoxy-2-pyridyl)ethyl]sulphinyl}-6-methyl-1H-benzimidazole (m.p. 144°–145° C. with decomposition) from 5-difluoromethoxy-2-{[1-(4-methoxy-2-pyridyl)ethyl]thio}-6-methyl-1H-benzimidazole and 5-(2-chloro-1,1,2-trifluoroethoxy)-2-{[1-(4-methoxy-2-pyridyl)ethyl]sulphinyl}-1H-benzimidazole (m.p.

139°–140° C. with decomposition, from ethyl acetate/diethyl ether) from 5-(2-chloro-1,1,2-trifluoroethoxy)-2-{[1-(4-methoxy-2-pryidyl)ethyl]thio}-1H-benzimidazole.

2.
5-Difluoromethoxy-2-[(4-methoxy-3-methyl-2-pyridyl)-methylthio]-4,6-dimethyl-1H-benzimidazole 2.0 g of 5-difluoromethoxy-4,6-dimethyl-1H-benzimidazole-2-thiol and 1.72 g of 2-chloromethyl-4-methoxy-3-methylpyridine hydrochloride are heated in 30 ml of 2-propanol for 4 h to the boil. This gives 3.6 g of the dihydrochloride of the title compound. This is dissolved in water and concentrated hydrochloric acid, the solution is clarified with activated charcoal, the product is precipitated with dilute sodium hydroxide solution and the precipitate is recrystallised from butanol. This gives 2.6 g (85%) of the title compound (m.p. 190°–191° C.).

Analogously, 5-difluoromethoxy-2-[(4-methoxy-2-pyridyl)methylthio]-4,6-dimethyl-1H-benzimidazole (m.p. 168°–169° C.) is obtained by reacting the thiol with 2-chloromethyl-4-methoxypyridine hydrochloride.

Analogously, 5-(2-chloro-1,1,2-trifluoroethoxy)-2-[(4-methoxy-2-pyridyl)methylthio]-1H-benzimidazole (m.p. 120° C., from ethyl acetate/toluene; dihydrochloride m.p. 197°–198° C.) is obtained by reaction of 5-(2-chloro-1,1,2-trifluoroethoxy)-1H-benzimidazole-2-thiol with 2-chloromethyl-4-methoxypyridine hydrochloride and 5-(2-chloro-1,1,2-trifluoroethoxy)-2-[(4-methoxy-3-methyl-2-pyridyl)-methylthio]-1H-benzimidazole (m.p. 111° C., from ethyl acetate) is obtained by reaction with 2-chloromethyl-4-methoxy-3-methylpyridine hydrochloride.

3.
4-Difluoromethoxy-5,6-dimethoxy-2-[(4-methoxy-3-methyl-2-pyridyl)methylthio]-1H-benzimidazole 1.0 g of 4-difluoromethoxy-5,6-dimethoxy-1H-benzimidazole-2-thiol, 0.75 g of 2-chloromethyl-4-methoxy-3-methylpyridine hydrochloride, 0.3 g of sodium hydroxide, 2 ml of water and 10 ml of ethanol are stirred for 2.5 h at 60° C. The mixture is poured onto 100 ml of water and cooled in an ice bath. This gives 1.3 g (87%) of the title compound (m.p. 177°–179° C., from diisopropyl ether).

Analogously, 4-difluoromethoxy-5,6-dimethoxy-2-[(4-methoxy-2-pyridyl)methylthio]-1H-benzimidazole (m.p. 112°–114° C.) is obtained by reacting the thiol with 2-chloromethyl-4-methoxypyridine hydrochloride.

Analogously, 5-difluoromethoxy-6-methoxy-2-{[1-(4-methoxy-2-pyridyl)ethyl]thio}-1H-benzimidazole (m.p. 128°–131° C., from toluene), 5-difluoromethoxy-2-{[1-(4-methoxy-2-pyridyl)ethyl]thio}-6-methyl-1H-benzimidazole (m.p. 183°–184° C., from ethyl acetate/toluene) and 5-(2-chloro-1,1,2-trifluoroethoxy)-2-{[1-(4-methoxy-2-pyridyl)ethyl]thio}-1H-benzimidazole (m.p. 120°–122° C., from toluene/diisopropyl ether) are obtained by reacting 5-difluoromethoxy-6-methoxy-1H-benzimidazole-2-thiol, 5-difluoromethoxy-6-methyl-1H-benzimidazole-2-thiol and 5-(2-chloro-1,1,2-trifluoroethoxy)-1H-benzimidazole-2-thiol with 2-(1-chloroethyl)-4-methoxypyridine hydrochloride.

4.
5-(2-Chloro-1,1,2-trifluoroethoxy)-2-[(4-methoxy-2-pyridyl)methylsulphinyl]-1H-benzimidazole 2.6 ml of 4N sodium hydroxide solution and a solution of 24 ml of sodium hypochlorite solution (6.6% of active chlorine) in 9.3 ml of 6N sodium hydroxide solution are added dropwise at −10° C. to a solution of 5.0 g of 5-(2-chloro-1,1,2-trifluoroethoxy)-2-[(4-methoxy-2-pyridyl)methylthio]-1H-benzimidazole in 50 ml of ethyl acetate, the mixture is stirred for a further 20 min-utes and the oxidising agent is destroyed with aqueous sodium thiosulphate solution. The organic layer is separated off and neutralised with potassium dihydrogen phosphate solution, and the organic layer is dried with magnesium sulphate, clarified with active charcoal and concentrated to dryness in vacuo. The residue is recrystallised from ethyl acetate and diisopropyl ether. This gives 2.9 g (56%) of the title compound of m.p. 109°–110° C. (decomposition).

Analogously, 5-[(2-chloro-1,1,2-trifluoro)ethoxy]-2-[(4-methoxy-3-methyl-2-pyridyl)methylsulfinyl]-1H-benzimidazole of m.p. 147°–148° C. (decomposition; sodium salt: m.p. 252°–254° C., decomposition) is obtained by oxidation of 5-[(2-chloro-1,1,2-trifluoro)ethoxy]-2-[(4-methoxy-3-methyl-2-pyridyl)methylthio]-1H-benzimidazole with sodium hypochlorite solution.

5.
5-Difluoromethoxy-2-[(4-methoxy-3-methyl-2-pyridyl)-methylsulphinyl]-4,6-dimethyl-1H-benzimidazole sodium salt and calcium salt 0.30 ml of 30% sodium methylate in methanol is added to 0.638 g of 5-difluoromethoxy-2-[(4-methoxy-3-methyl-2-pyridyl)methylsulphinyl]-4,6-dimethyl-1H-benzimidazole in 10 ml of ethanol, and the mixture is stirred until the compound is dissolved. The mixture is concentrated in a rotary evaporator and one half of the residue is treated with 15 ml of water, concentrated to dryness in vacuo and dried in a high vacuum at 70°–120° C. This gives the sodium salt of m.p. 250°–252° C. (decomposition).

The other half is dissolved in 15 ml of water and precipitated with a solution of 60 mg of calcium chloride in 5 ml of water, and the precipitate is washed with water and dried in a high vacuum at 70° C. This gives the calcium salt of m.p. 213°–215° C. (decomposition).

6.
5-Difluoromethoxy-2-[(3,4-dimethoxy-2-pyridyl)methylsulphinyl]-4,6-dimethyl-1H-benzimidazole 5 ml of a 0.2N solution of m-chloroperoxybenzoic acid in methylene chloride are added dropwise at −40° C. to a solution of 0.39 g (1 mmol) of 5-difluoromethoxy-2-[(3,4-dimethoxy-2-pyridyl)methylthio]-4,6-dimethyl-1H-benzimidazole in 20 ml of methylene chloride, and the mixture is stirred for 15 minutes. 0.5 ml of triethylamine are then added and the reaction mixture is poured into 20 ml of a 1:1 mixture of 5% sodium carbonate solution and 5% sodium thiosulphate solution. After phase separation, the aqueous phase is extracted twice more with 30 ml of methylene chloride each time, and the combined organic phases are washed with sodium carbonate solution, dried over magnesium sulphate, filtered and concentrated to 2 ml. After crystallisation from diisopropyl ether, the crystals are filtered off and dried to constant weight. This gives 0.3 g (74% of theory) of the title compound as a colourless solid of m.p. 163°–164° C. (decomposition).

Analogously, 5-[(2-chloro-1,1,2-trifluoro)ethoxy]-2-[(3,4-dimethoxy-2-pyridyl)methylsulphinyl]-1H-benzimidazole is obtained by oxidation of 5-[(2-chloro-1,1,2-trifluoro)ethoxy]-2-[(3,4-dimethoxy-2-pyridyl)methylthio]-1H-benzimidazole with m-chloroperoxybenzoic acid.

7.
5-Difluoromethoxy-2-[(3,4-dimethoxy-2-pyridyl)methylthio]-4,6-dimethyl-1H-benzimidazole 0.45 g (1.8 mmol) of 5-difluoromethoxy-4,6-dimethyl-2-mercaptobenzimidazole and 0.41 g (1.8 mmol) of 2-chloromethyl-3,4-dimethoxypyridinium chloride are heated to the boil under reflux in 20 ml of dry isopropanol. Temporarily, a clear solution is formed, from which a colourless solid precipitates. After 3 h, the mixture is allowed to cool and is filtered, the filter residue is washed with isopropanol and then dissolved in water, and the pH of the solution is adjusted to 9 with 1N sodium hydroxide solution, with stirring. The precipitated product is filtered off, once suspended in 20 ml of water, filtered off again and washed until neutral. After drying to constant weight in vacuo, this gives 0.50 g (69% of theory) of the title compound as a colourless solid; m.p. 137°–138° C.

Analogously, 5-[(2-chloro-1,1,2-trifluoro)ethoxy]-2-[(3,4-dimethoxy-2-pyridyl)methylthio]-1H-benzimidazole (m.p. 99°–102° C.) is obtained by reacting 5-(2-chloro-1,1,2-trifluoroethoxy)-2-mercaptobenzimidazole with 2-chloromethyl-3,4-dimethoxypyridinium chloride.

8.
5-(1,1,2,2-Tetrafluoroethoxy)-2-{[1-(4-methoxy-2-pyridyl)ethyl]sulphinyl}-1H-benzimidazole 9.8 g of 80% m-chloroperoxybenzoic acid in 200 ml of dichloromethane are added dropwise at −65° C. to a solution of 19.5 g of ±-5-(1,1,2,2-tetrafluoroethoxy)-2-{[1-(4-methoxy-2-pyridyl)ethyl]thio}-1H-benzimidazole in 1.5 l of dichloromethane. The reaction mixture is stirred for a further 2 h at −40° C. and then stirred into a sodium carbonate solution. The organic phase is separated off, and the aqueous phase is extracted once more with dichloromethane. The combined organic phases are dried over sodium sulphate and concentrated. A sparingly soluble diastereomer thus crystallises. The other diastereomer remains in the mother liquor and can either be purified by chromatography or can, by leaving it to stand, preferably in the presence of bases, be rearranged into the less soluble diastereomer. Recrystallisation of sparingly soluble product from ethyl acetate/diisopropyl ether gives 10 g (51%) of the title compound of m.p. 156°–157° C.

Analogously, 2,2-difluoro-6-{[1-(4-methoxy-2-pyridyl)ethyl]sulphinyl}-5H-[1,3]-dioxolo[4,5-f]benzimidazole (m.p. 170° C.) and 5-(2,2,2-trifluoroethoxy)-2-{[1-(4-methoxy-2-pyridyl)ethyl]sulphinyl}-1H-benzimidazole (oil) are respectively obtained by oxidation of (±)-2,2-difluoro-6-{[1-(4-methoxy-2-pyridyl)ethyl]thio}-5H-[1,3]-dioxolo[4,5-f]benzimidazole and (±)-5-(2,2,2-trifluoroethoxy)-2-{[1-(4-methoxy-2-pyridyl)ethyl]thio}-1H-benzimidazole with m-chloroperoxybenzoic acid.

9.
(±)-2,2-Difluoro-6-{[1-(4-methoxy-2-pyridyl)ethyl]thio}-5H-[1,3]-dioxolo[4,5-f]benzimidazole 4 g of 2,2-difluoro-5H-[1,3]-dioxolo[4,5-f]benzimidazole-6-thiol, 3.6 g of (±)-2-(1-chloroethyl)-4-methoxy-pyridine hydrochloride, 1.4 g of sodium hydroxide, 3 ml of water and 50 ml of ethanol are stirred for 4 h at 65° C. The reaction mixture is concentrated to dryness, the residue is dissolved in 100 ml of 2N hydrochloric acid, impurities are extracted by shaking with ethyl acetate, and the aqueous phase is adjusted with sodium hydroxide solution to pH 10 and extracted with ethyl acetate. The organic phase is dried and concentrated. Recrystallisation from toluene gives 4.3 g (80.5%) of the title compound of m.p. 173°–175° C.

Analogously, (±)-5-(1,1,2,2-tetrafluoroethoxy)-2-{[1-(4-methoxy-2-pyridyl)ethyl]thio}-1H-benzimidazole (m.p. 78°–81° C.) and (±)-5-(2,2,2-trifluoroethoxy)-2-{[1-(4-methoxy-2-pyridyl)ethyl]thio}-1H-benzimidazole (oil) are respectively obtained by reacting the pyridine hydrochloride with 2-mercapto-5-(1,1,2,2-tetrafluoroethoxy)-1H-benzimidazole and 2-mercapto-5-(2,2,2-trifluoroethoxy)-1H-benzimidazole.

Starting compounds
A. Pyridines

The pyridines are prepared analogously to the processes described in German Offenlegungsschrift No. 3,404,610, EP-A No. 0,005,129 and EP-A No. 0,080,602, or as follows:

A1. 2-Chloromethyl-4,5-dimethoxy-pyridinium chloride (a) 2-Chloromethyl-4,5-dimethoxy-pyridinium chloride 3 ml of thionyl chloride, dissolved in 10 ml of methylene chloride, are added dropwise to a solution, cooled to 0° C., of 5 g of 2-hydroxymethyl-4,5-dimethoxypyridine in 40 ml of methylene chloride in the course of one hour, the reaction mixture is then stirred at 20° C. for 4 hours, during which it becomes red-colored, 5 ml of toluene are added and the mixture is concentrated completely on a rotary evaporator (30° C./5 mbar). The oily residue is dissolved in 50 ml of warm isopropanol and the solution is clarified with a little Tonsil ®, filtered and concentrated again. The residue is taken up in 10 ml of toluene and the solution is made to crystallize with petroleum ether. After cooling in an ice-bath, the precipitate is filtered off with suction, washed with petroleum ether and dried. 4.6 g (70% of theory) of the title compound 2-chloromethyl-4,5-dimethoxy-pyridinium chloride are obtained as a colourless soldi; decomp. at 160°–61° C.

(b) 2-Hydroxymethyl-4,5-dimethoxy-pyridine 19 g of 4,5-dimethoxy-2-methylpyridine 1-oxide are metered into 60 ml of acetic anhydride, warmed to 80° C., in the course of 30 minutes in a manner such that the temperature does not rise above 100° C. After a further 45 minutes at 85° C., excess acetic anhydride is distilled off in vacuo and the oily dark residue, which essentially consists of the intermediate 2-acetoxymethyl-4,5-dimethoxypyridine is stirred with 80 ml of 2N sodium hydroxide solution at 80° C. for 1 hour. After dilution with 80 ml of water and cooling, the mixture is extracted eight times with 100 ml of methylene chloride each time, the combined organic phases are washed twice with 1N sodium hydroxide solution, dried and concentrated and the crystalline, brownish residue is recrystallized from toluene. 14 g (74% of theory) of 2-hydroxymethyl-4,5-dimethoxy-pyridine of m.p. 122°–24° C. are obtained.

(c) 4,5-dimethoxy-2-methylpyridine 1-oxide 20 ml of a 30% strength sodium methylate solution are added dropwise to a suspension of 16.9 g of 5-methoxy-2-methyl-4-nitropyridine 1-oxide in 170 ml of dry methanol and the mixture is stirred at 20° C. for 15 hours and then at 50° C. for 4 hours. The pH is brought to 7 by careful addition of concentrated sulphuric acid, while cooling with ice, the mixture is concentrated, the residue is extracted by stirring with 200 ml of methylene chloride, the insoluble constituents are filtered off, 10 ml of toluene are added and the mixture is concentrated to dryness again. 15.2 g (98% of theory) of 4,5-dimethoxy-2-methylpyridine 1-oxide are obtained as colourless crystals of m.p. 118°–121° C.

(d) 5-Methoxy-2-methyl-4-nitropyridine 1-oxide 21.2 g of 5-methoxy-2-methylpyridine 1-oxide are metered into 35 ml of 65% strength nitric acid, warmed to 60° C., in a manner such that the temperature of the reaction mixture does not rise above 80° C. The mixture is stirred at 80° C. for 1 hour, a further 13 ml of 100% strength nitric acid are added to bring the reaction to completion and the mixture is stirred at 60°–70° C. for a further 2 hours. For working up, the mixture is poured onto 300 g of ice. The yellow precipitate which has separated out is filtered off over a suction filter, washed with water and dried. The dry solid is boiled up with 200 ml of methylene chloride, filtered off and dried. Further TLC-pure product is isolated by concentration of the filtrate. 22.3 g (87% of theory) of 5-methoxy-2-methyl-4-nitropyridine 1-oxide of m.p. 201°–202° C. are obtained; yellow crystals.

(e) 5-Methoxy-2-methylpyridine 1-oxide 120 g pf 30% strength hydrogen peroxide solution are added dropwise to a solution of 60.9 g of 5-methoxy-2-methylpyridine in 300 ml of glacial acetic acid at 60° C. in the course of 1 hour and the mixture is subsequently stirred for 3 hours. After destruction of excess percompounds by addition of active manganese dioxide, the mixture is filtered, the filtrate is concentrated, the residue is clarified hot in 500 ml of ethyl acetate, the mixture is concentrated again and the residue is distilled under 0.3 mbar. 54 g (77% of theory) of 5-methoxy-2-methylpyridine 1-oxide are obtained as a rapidly solidifying oil (b.p. 130° C.); m.p. 80°–84° C.

(f) 5-Methoxy-2-methylpyridine 150 ml of 3-hydroxy-6-methylpyridine are metered into a solution of 84 g of potassium hydroxide in 400 ml of methanol and 500 ml of dimethyl sulphoxide in the course of one hour. After removal of the methanol on a rotary evaporator, 213 g of methyl iodide, dissolved in 100 ml of dimethyl sulphoxide, are added dropwise, while cooling with ice, and the reaction mixture is stirred at 20° C. for 15 hours and subjected to steam distillation. The distillate is extracted continuously in the extractor with methylene chloride and the extract is concentrated. 85 g (56% of theory) of 5-methoxy-2-methylpyridine are obtained as a colourless oil.

A2. 2-Chloromethyl-4,5-dimethoxy-3-methylpyridinium chloride

(a) 2-Chloromethyl-4,5-dimethoxy-3-methylpyridinium chloride 3.45 g (99% of theory) of the title compound are obtained as colourless crystals by the procedure described in Example A1a) by reaction of 2.7 g of 2-hydroxymethyl-4,5-dimethoxy-3-methylpyridine with 4 g of thionyl chloride in 25 ml of methylene chloride, after a reaction time of 1 hour and after a simplified method of working up, in particular by addition of 10 ml of toluene, removal of the methylene chloride and excess thionyl chloride by distillation, removal of the crystals precipitated by filtration with suction and drying; decomp. at 125°–26° C.

(b) 2-Hydroxymethyl-4,5-dimethoxy-3-methylpyridine 4.5 of 4,5-dimethoxy-2,3-dimethylpyridine 1-oxide are warmed to 110° C. in 20 ml of acetic anhydride in the course of 30 minutes and the mixture is then concentrated on a rotary evaporator. The oily residue, which consists of the intemediate 2-acetoxymethyl-4,5-dimethoxy-3-methylpyridine, is stirred in 30 ml of 3N sodium hydroxide solution at 80° C. for 2 hours, the mixture is extracted, after cooling, five times with 30 ml of methylene chloride each time, the combined organic phases are washed twice with 2N sodium hydroxide solution, dried and concentrated and the residue is stirred with petroleum ether, filtered off with suction and dried. 4.0 g (89% of theory) of 2-hydroxymethyl-4,5-dimethoxy-3-methylpyridine of m.p. 91°–92° C. are obtained.

(c) 4,5-Dimethoxy-2,3-dimethylpyridine 1-oxide 6.3 g of 4,5-dimethoxy-2,3-dimethylpyridine are dissolved in 120 ml of methylene chloride, 20 g of m-chloroperoxybenzoic acid are added successively and the mixture is stirred first at 20° C. for 2 hours and then at 40° C. for 4 hours. After addition of 20 ml of 5N sodium hydroxide solution, the mixture is washed three times with a mixture of 5% strength sodium thiosulphate solution and 5% strength sodium carbonate solution, the aqueous phases are back-extracted twice with methylene chloride and the combined organic phases are dried over magnesium sulphate and concentrated. 4.6 g (66% of theory) of 4,5-dimethoxy-2,3-dimethylpyridine 1-oxide are obtained. The Rf value in methylene chloride/methanol 19:1 is 0.25.

(d) 4,5-Dimethoxy-2,3-dimethylpyridine 7.4 g (74% of theory) of 4,5-dimethoxy-2,3-dimethylpyridine are obtained as a colourless, gradually crystallising oil of m.p. 36°–38° C. by the procedure described in Example A1f) by reaction of 9.18 g of 5-hydroxy-4-methoxy-2,3-dimethylpyridine in 50 ml of dimethyl sulphoxide first with 3.6 g of sodium hydroxide and then with 8.95 g of methyl iodide.

(e) 5-Hydroxy-4-methoxy-2,3-dimethylpyridine 1,000 g of 4-methoxy-2,3-dimethylpyridine 1-oxide are metered into 3 l of acetic anhydride at 100° C. in the course of 7 hours while stirring, and the mixture is subsequently stirred at 100° C. for a further 3 hours. The mixture is allowed to cool and is concentrated completely at 70° C./10 mbar and the residue is then distilled under $10^{-2}$ mbar. The fraction with a boiling range from 95° to 145° C. (mixture of the intermediate 5-acetoxy-4-methoxy-2,3-dimethylpyridine and 2-acetoxymethyl-4-methoxy-3-methylpyridine) is removed (952 g) and added to 3.5 l of 2N sodium hydroxide solution, warmed to 50° C., in the course of 30 minutes.

The mixture is stirred at 50° C. until a clear solution is formed (about 3 hours) and is allowed to cool and is extracted three times with 1 l of methylene chloride each time. The combined organic phases are back-extracted twice with 0.5 l of 1N sodium hydroxide solution each time and the combined aqueous phases are then brought to pH 7.5 with half-concentrated hydrochloric acid, with stirring. The solid which has precipitated out is filtered off, rinsed and dried to constant weight. 5-Hydroxy-4-methoxy-2,3-dimethylpyridine of m.p. 274°–76° C. is obtained.

A3. 2-Chloromethyl-3,4-dimethoxy-pyridine chloride (a) 2-Chloromethyl-3,4-dimethoxy-pyridinium chloride 4.2 g (93% of theory) of the title compound are obtained as a colourless solid of m.p. 151°–152° C. (decomp.) by the procedure described in Example A1a by reaction of 3.38 g of 2-hydroxymethyl-3,4-dimethoxypyridine with 2 ml of thionyl chloride in 30 ml of methylene chloride, after a reaction time of 2.5 hours and after the type of working up described in Example A2a.

(b) 2-Hydroxymethyl-3,4-dimethoxypyridine

After adding 15 ml of 2N sodium hydroxide solution, 4.8 g of 2-acetoxymethyl-3,4-dimethoxypyridine are stirred vigorously at 80° C., whereupon a homogeneous solution forms from the initial two-phase mixture. After 2 hours, the solution is allowed to cool and is extracted five times with 30 ml of methylene chloride each time, the combined organic phases are washed twice with 5 ml of 0.3N sodium hydroxide solution each time, dried over potassium carbonate, filtered and concentrated and the distillation residue is stirred with petroleum ether. 3.6 g (96% of theory) of 2-hydroxymethyl-3,4-dimethoxypyridine are obtained as a colourless solid of m.p. 87°–89° C.

(c) 2-Acetoxymethyl-3,4-dimethoxypyridine 4.8 g (28 mmol) of 3,4-dimethoxy-2-methylpyridine 1-oxide are metered into 25 ml of acetic anhydride at 85° C. in the course of one hour, the mixture is stirred at the same temperature for one hour and concentrated completely in vacuo and the brown oily residue is distilled in a bulb type still under 1 Pa. 5.3 g (90% of theory) of 2-acetoxymethyl-3,4-dimethoxypyridine are obtained; b.p. 125°–130° C.

(d) 3,4-Dimethoxy-2-methylpyridine 1-oxide 4.5 g (25 mmol) of 3-methoxy-2-methyl-4-nitropyridine 1-oxide are stirred at 40° C. in 75 ml of dry methanol, after addition of 4.7 ml of 30% strength sodium methylate solution, for 16 hours. The mixture is then cooled, brought to pH 7 with concentrated sulphuric acid, filtered and concentrated completely in vacuo, the oily, reddish residue is taken up in 50 ml of toluene, the mixture is filtered again to remove insoluble constituents and the filtrate is concentrated to dryness. The yellow oily residue crystallises in an ice-bath and is finally extracted by stirring with 30 ml of petroleum ether (50/70) at 40° C. Filtration and drying in a desiccator gives 5.2 g (88% of theory) of 3,4-dimethoxy-2-methylpyridine 1-oxide in the form of pale yellow crystals of m.p. 111°–113° C.

(e) 3-Methoxy-2-methyl-4-nitropyridine 1-oxide 8 ml of concentrated nitric acid are added in four portions of 2 ml each to 5.4 g of 3-methoxy-2-methylpyridine 1-oxide in 12 ml of glacial acetic acid at 80° C. in the course of 6 hours, the mixture is stirred at the same temperature overnight, a further 8 ml of nitric acid are added in three portions in the course of 6 hours and the mixture is stirred for a further 15 hours. After cooling, the mixture is poured onto ice (40 g) and brought to pH 6 with 10N sodium hydroxide solution, the by-product (3-methoxy-2-methyl-4-nitropyridine) which has precipitated out is filtered off and the filtrate is extracted four times with 50 ml of methylene chloride. After drying, the combined organic phases are concentrated completely and the residue is recrystallised from a little methylene chloride/petroleum ether. 4.2 g (57% of theory) of the title compound are obtained in the form of yellow crystals of m.p. 103°–104° C.

(f) 3-Methoxy-2-methylpyridine 1-oxide 15.3 g (0.124 mol) of 3-methoxy-2-methylpyridine are dissolved in 100 ml of glacial acetic acid, and 40 ml of 30% strength hydrogen peroxide are added in 4 portions at 80° C. in the course of 6 hours. The mixture is stirred for a further 3 hours and then concentrated in vacuo (1.5 kPa), and two 50 ml portions of acetic acid are added, the mixture being concentrated completely after each addition. Following negative detection of percompounds, the mixture is distilled in a bulb tube oven. The fraction which distils at 120° C. (1.5 Pa) is extracted by stirring in a little diethyl ether and the solid is filtered off and dried. 12 g (60% of theory) of 3-methoxy-2-methylpyridine 1-oxide are obtained in the form of colourless crystals of m.p. 72°–78° C.

(g) 3-Methoxy-2-methylpyridine 15.5 g (90% of theory) of 3-methoxy-2-methylpyridine are obtained as a colourless oil by the procedure described in Example A1f by reaction of 13.7 g (125 mmol of 3-hydroxy-2-methylpyridine with 9.2 ml of methyl iodide, with the addition of 46 ml of 3M methanolic potassium hydroxide solution and after a reaction time of 3 hours.

A4. 2-(1-Chloroethyl)-4-methoxy-pyridine hydrochloride (a) 2-(1-Chloroethyl)-4-methoxy-pyridine hydrochloride 36 ml of thionyl chloride are added dropwise to a cooled suspension of 57 g of (±)-1-[4-methoxy-2-pyridyl]ethanol in 400 ml of dichloromethane, in such a way that the internal temperature does not exceed 15° C. The mixture is then heated under reflux for 2.5 h, treated with 300 ml of toluene and concentrated to 150 ml. The reaction product which has precipitated is filtered off with suction and rinsed with cold toluene and petroleum ether. This gives 76.4 g (98.2%) of the title compound of m.p. 113°–116° C.

(b) (+)-1-(4-Methoxy-2-pyridyl)-ethanol 114 g of (+)-1-[4-methoxy-2-pyridyl]-ethyl acetate are added dropwise at 70° C. to 220 ml of 4N sodium hydroxide solution. The mixture is then stirred for a further 2 h at 75° C., cooled and extracted with four times 200 ml of dichloromethane. The organic phase is washed with 2N sodium hydroxide solution and water, dried over sodium sulphate and concentrated to dryness. After thorough stirring with 250 ml of diisopropyl ether, this gives 64 g (72%) of the title compound of m.p. 92° C.

(c) (±)-1-[4-methoxy-2-pyridyl]-ethyl acetate 171 g of 2-ethyl-4-methoxy-pyridine N-oxide are added dropwise within 3 h to 312 ml of acetic anhydride heated to 90° C., in such a way that the internal temperature does not exceed 115° C. The mixture is then left to stand for a further 2.5 h at 100° C., and excess acetic anhydride is stripped off. Distillation of the residue gives 171 g (78%) of the title compound of b.p. 100° C./1 Pa.

(d) 2-Ethyl-4-methoxypyridine N-oxide 236 ml of 30% sodium methylate solution (in methanol) are added dropwise within 2.5 h to a suspension of 192 g of 4-nitro-2-ethylpyridine n-oxid in 1.1 l of absolute methanol, in such a way that the internal temperature does not exceed 30° C. The mixture is then stirred for a further 12 h, adjusted with about 10 ml of concentrated sulphuric acid to pH 6.5-7, filtered and concentrated. The residue is washed three times with hot toluene, and the extract is clarified with a little Tonsil. By concentrating, a residue of 172 g of the title compound is obtained as an oil.

B. Benzimidazoles

B1.
5-(1,1,2,2-Tetrafluoroethoxy)-1H-benzimidazole-2-thiol (a) 55 g of 1-nitro-4-(1,1,2,2-tetrafluoroethoxy)benzene are hydrogenated in 300 ml of ethanol on 0.5 g of 10% palladium-on-carbon in a circulating hydrogenation apparatus under atmospheric pressure for 1 h at 20°-45° C., the catalyst is filtered off and the solution is concentrated in vacuo at 40° C. The 4-(1,1,2,2-tetrafluoroethoxy)-aniline is diluted with 100 ml of glacial acetic acid and 23 ml of acetic anhydride are added dropwise at room temperature, 2 ml of water are added after 30 minutes, after a brief period the solution is concentrated in vacuo at 50° C., and 500 ml of ice water are added. This gives 56 g (97%) of N-[4-(1,1,2,2-tetrafluoroethoxy)phenyl]acetamide of m.p. 121°-122° C.

(b) 55 g of the above compound are dissolved in 380 ml of dichloromethane, 55 ml of 100% nitric acid are added dropwise within 10 min. at room temperature and the mixture is stirred for a further 6 h. The organic solution is then washed with aqueous sodium carbonate solution and water, dried with magnesium sulphate and concentrated. This gives 65 g (100%) of N-[2-nitro-4-(1,1,2,2-tetrafluoroethoxy)phenyl]acetamide of m.p. 80°-81° C. (from cyclohexane).

(c) 63 g of the above compound are dissolved in 450 ml of methanol, 106 ml of 6M sodium hydroxide solution are added dropwise at room temperature, the mixture is cooled in an ice bath and 53 g (98%) of 2-nitro-4-(1,1,2,2-tetrafluoroethoxy)-aniline (m.p. 85°-86° C.) are precipitated by dropwise addition of 900 ml of water.

(d) 33 g of the above compound are hydrogenated in about 600 ml of isopropanol on 1 g of 10% palladium-on-carbon in a circulating hydrogenation apparatus under normal pressure at room temperature. The catalyst is filtered off with suction, and 34 g (89%) of 4-(1,1,2,2-tetrafluoroethoxy)-1,2-phenylenediamine dihydrochloride of m.p. 275°-276° C. (decomposition) are precipitated by means of 4M hydrogen chloride in ether.

(e) 330 ml of ethanol, 60 ml of water, 8.9 g of sodium hydroxide and 23 g of potassium O-ethyl dithiocarbonate (recrystallised from isopropanol) are added to 33 g of the above compound and the mixture is heated to the boil under reflux for 15 h. 1.2 l of ice water are added, the pH is adjusted to 13-14 with sodium hydroxide solution, the solution is clarified with active charcoal and the product is precipitated with dilute hydrochloric acid up to pH 3.5. This gives 27 g (91%) of the title compound of m.p. 316°-319° C. (from isopropanol).

B2. 5-Trifluoromethoxy-1H-benzimidazole-2-thiol

Analogously to Example B1e, the title compound of m.p. 305°-307° C. (decomposition, from toluene) is obtained in 75% yield by reacting 4-trifluoromethoxy-1,2-phenylenediamine dihydrochloride (cf. C.A. 55, 23408d, 1961) with potassium O-ethyl dithiocarbonate and sodium hydroxide solution in ethanol.

B3. 5-(2,2,2-Trifluoroethoxy)-1H-benzimidazole-2-thiol (a) 50 g of 1-(2,2,2-trifluoroethoxy)-4-nitrobenzene (Synthesis 1980, page 727) are hydrogenated and acetylated analogously to Example B1a. This gives 50 g (95%) of N-[4-(2,2,2-trifluoroethoxy)phenyl]-acetamide (m.p. 140°-141° C.).

(b) 42 g of the above compound are stirred with 9.7 ml of 100% nitric acid in 290 ml of glacial acetic acid for 18 h at room temperature and the product is precipitated with water. This gives 47 g (94%) of N-[2-nitro-4-(2,2,2-trifluoroethoxy)-phenyl]-acetamide (m.p. 117°-118° C.).

(c) 47 g of the above compound are hydrogenated analogously to Example B1c and 38.7 g (97%) of 2-nitro-4-(2,2,2-trifluoroethoxy)-aniline (m.p. 84°-85° C.) are obtained.

(d) 37 g of the above compound are hydrogenated analogously to Example B1d and 41 g (94%) of 4-(2,2,2-trifluoroethoxy)-1,2-phenylenediamine dihydrochloride of m.p. 230°-233° C. (decomposition) are obtained.

(e) Analogously to Example B1e, 30 g (94%) of the title compound (m.p. 288°-290° C.) are obtained from 36 g of the above compound.

B4.
5-Chlorodifluoromethoxy-1H-benzimidazole-2-thiol (a) 10.0 g of N-[4-(chlorodifluoromethoxy)phenyl]acetamide (m.p. 101°-103° C., from 4-chlorodifluoromethoxyaniline and acetic anhydride) and 12.3 ml of 100% nitric acid are stirred in 80 ml of dichloromethane for 4 h at 20° C. The mixture is neutralised with aqueous potassium bicarbonate solution, the organic layer is concentrated, and 11.4 g (96%) of N-(4-chlorodifluoromethoxy-2-nitrophenyl)-acetamide (m.p. 89°-91° C.) are obtained.

(b) 8.6 ml of a 30% solution of sodium methylate in methanol are added dropwise at 5° C. to 10.5 g of the above compound in 200 ml of methanol, the mixture is stirred for 2 h without cooling, ice water is added, the pH is adjusted to 8 and 8.7 g (97%) of 4-chlorodifluoromethoxy-2-nitroaniline (m.p. 40°-42° C.) are obtained.

(c) 8.5 g of the above compound are hydrogenated on 0.8 g of 10% palladium-on-carbon under normal pressure in 200 ml of methanol, concentrated hydrochloric acid is added, the mixture is filtered and concentrated, and the residue is stirred up with diisopropyl ether. This gives 8.5 g (97%) of 4-chlorodifluoromethoxy-1,2-phenylenediamine dihydrochloride.

(d) Analogously to Example B1e, 6.3 g (72%) of the title compound of m.p. 268°–270° C. (decomposition) are obtained from 8.5 g of the above compound.

B5. 5-Difluoromethoxy-1H-benzimidazole-2-thiol (a) 11.8 g of N-(4-difluoromethoxyphenyl)-acetamide [L. M. Jagupol'skii et al., J. General Chemistry (USSR) 39, 190 (1969)] are stirred in 200 ml of dichloromethane with 12.1 ml of 100% nitric acid for 1.5 h at room temperature. Analogously to Example B1b, this gives 13.3 g (92%) of N-[(4-difluoromethoxy-2-nitro)phenyl]-acetamide (m.p. 71°–73° C.).

(b) Analogously to Example B4b, 4-difluoromethoxy-2-nitroaniline (m.p. 68°–70° C.) is obtained from this in 96% yield.

(c) Analogously to Example B4c, 4-difluoromethoxy-1,2-phenylenediamine dihydrochloride is obtained in 94% yield.

(d) Analogously to Example B1e, the title compound of m.p. 250°–252° C. (from 2-propanol) is obtained in 78% yield.

B6. 5,6-Bis-(difluoromethoxy)-1H-benzimidazol-2-thiol (a) 275 g of chlorodifluoromethane are passed at 50°–55° C. into a solution of 100 g of pyrocatechol, 220 g of sodium hydroxide and 60 g of sodium dithionite in 500 ml of water and 400 ml of dioxane, analogously to L. N. Sedova et al., Zh. Org. Khim. 6, 568 (1970). After distillation at 61°–62° C./1.0–1.1 pKa, this gives a mixture of 1,2-bis-(difluoromethoxy)-benzene and 2-difluoromethoxyphenol, which are separated by chromatography on silica gel by means of cyclohexane/ethyl acetate (4:1).

(b) A solution of 15 g of 1,2-bis-(difluoromethoxy)-benzene and 15 ml of 100% nitric acid in 150 ml of dichloromethane is stirred for 7 h at room temperature. The mixture is neutralised with potassium bicarbonate solution, and the organic phase is separated off and subjected to chromatography on silica gel by means of cyclonhexane/ethyl acetate (4:1). This gives 1,2-bis-(difluoromethoxy)-4-nitrobenzene. The latter is hydrogenated and acetylated analogously to Example B1a, to give N-[3,4-bis-(difluoromethoxy)phenyl]-acetamide (m.p. 81°–83° C.). Analogously to Example B1, this then gives N-[4,5-bis-(difluoromethoxy)-2-nitrophenyl]-acetamide (m.p. 65°–67° C., N-[4,5-bis-(difluoromethoxy)-2-nitro]-aniline (m.p. 107°–109° C.), 4,5-bis-(difluoromethoxy)-1,2-phenylenediamine dihydrochloride and the title compound of m.p. 285°–287° C. (decomposition; from 2-propanol).

B7.
5-Difluoromethoxy-6-methoxy-1H-benzimidazole-2-thiol (a) About 58 g of chlorodifluoromethane are passed at 60° C. into a solution of 55.5 g of guajacol and 130 g of sodium hydroxide in 300 ml of water and 300 ml of dioxane. The mixture is filtered at 10° C., and the organic layer is separated off, dried with anhydrous potassium carbonate and distilled. This gives 56 g (73%) of 1-difluoromethoxy-2-methoxybenzene of b.p. 75°–76° C./0.9 kPa.

(b) A solution of 33.8 ml of 100% nitric acid in 90 ml of dichloromethane is added dropwise at 0°–5° C. to a solution of 47 g of the above compound in 230 ml of dichloromethane, 250 ml of ice water are added after 30 minutes, and the mixture is neutralised with potassium bicarbonate. The dried organic phase is concentrated in vacuo and the residue is recrystallised from cyclohexane. This gives 53 g (90%) of 1-difluoromethoxy-2-methoxy-5-nitrobenzene (m.p. 48°–49° C.). This is hydrogenated and acetylated analogously to Example B1a. This gives N-(3-difluoromethoxy-4-methoxyphenyl)acetamide (m.p. 129°–130° C.) in 90% yield.

(c) 46 g of the above compound are nitrated analogously to the above instructions with 33 ml of 100% nitric acid in dichloromethane. This gives N-(5-difluoromethoxy-4-methoxy-2-nitrophenyl)acetamide (m.p. 116°–117° C.) in 99% yield.

(d) 54 g of the above compound are stirred at room temperature in 810 ml of methanol for 1 h with 44.8 ml of 30% methanolic sodium methylate solution. The mixture is concentrated in vacuo, ice water and glacial acetic acid up to pH 8 are added, and 5-difluoromethoxy-4-methoxy-2-nitroaniline (m.p. 144°–145° C.) is obtained in 99% yield.

(e) 25 g of the above compound are hydrogenated in 300 ml of methanol on 1.25 g of 10% palladium-on-carbon correspondingly to Example B1d. This gives 26 g (88%) of 3-difluoromethoxy-4-methoxy-1,2-phenylenediamine dihydrochloride of m.p. 218°–220° C. (decomposition).

(f) 25 g of the above compound are reacted with 19 g of potassium O-ethyl dithiocarbonate correspondingly to Example B1e. This gives 20 g (89%) of the title compound of m.p. 280°–282° C. (decomposition; from 2-propanol).

B8.
5-Difluoromethoxy-6-fluoro-1H-benzimidazole-2-thiol (a) Analogously to Example B7a, 1-difluoromethoxy-2-fluorobenzene (b.p. 76° C/10 kPa; $n_D^{20}=1.4340$) is obtained from 2-fluorophenol and chlorodifluoromethane.

(b) 38.4 ml of 100% nitric acid are added dropwise at −10° C. to 30 g of the above compound in 300 ml of dichloromethane, and the mixture is stirred for 1 h at −10° C. and 2 h at 0° C. Ice water is added, and the mixture is rendered neutral and subjected to chromatography on silica gel with ethyl acetate/cyclohexane (4:1). This gives 34 g of an oil which contains about 90% of 1-difluoromethoxy-2-fluoro-4-nitrobenzene and 10% of 1-difluoromethoxy-2-fluoro-5-nitrobenzene (NMR spectrum).

(c) 30 g of the above mixture are hydrogenated and acetylated analogously to Example B1a. After recrystallisation from toluene, this gives 21 g (65%) of N-(4-difluoromethoxy-3-fluorophenyl)acetamide of m.p. 112°–113° C.

(d) 22.5 ml of 100% nitric acid are added dropwise at 20° C. within 30 min. to 20 g of the above compound in 200 ml of dichloromethane, and the mixture is stirred for a further 15 h at room temperature. Analogously to Example B7c, this gives N-(4-difluoromethoxy-5-fluoro-2-nitrophenyl)acetamide of m.p. 72°–74° C. (from cyclohexane) in 89% yield. By stirring for several hours with 1M hydrochloric acid in methanol at 60° C., 4-difluoromethoxy-5-fluoro-2-nitroaniline of m.p. 95°–97.5° C. is obtained in 95% yield and, analogously to Example B7e, 4-difluoromethoxy-5-fluoro-1,2-phenylenediamine dihydrochloride (decomposition from 210° C.) is obtained in 85% yield.

(e) 15 g of the above compound are reacted with 11.8 g of potassium O-ethyl dithiocarbonate correspondingly to Example B1e. This gives 11.1 g (84%) of the title compound of m.p. 275°–276° C. (decomposition; from 2-propanol).

B9.
2,2-Difluoro-5H-[1,3]-dioxolo[4,5-f]benzimidazole-6-thiol (a) 30 g of 4-amino-2,2-difluoro-5-nitro-1,3-benzodioxole are hydrogenated in 300 ml of methanol on 0.5 g of 10% palladium-on-carbon in a circulating hydrogenation apparatus under atmospheric pressure and at room temperature, 2.5 equivalents of methanolic hydrogen chloride solution are added, the mixture is filtered, the solution is concentrated in vacuo, 2-propanol and ether are added, and 35 g (97%) of 2,2-difluoro-1,3-benzodioxole-4,5-diamine dihydrochloride of m.p. 232°–233° C. (decomposition) are obtained.

(b) 24 g of potassium O-ethyl dithiocarbonate (recrystallised from 2-propanol) and 9.2 g of sodium hydroxide in 55 ml of water are added to 30 g of the above compound in 300 ml of ethanol, and the mixture is heated under reflux for 15 h to the boil. The mixture is poured onto 1.5 l of water, adjusted to pH 14 with sodium hydroxide solution and clarified with active charcoal, the product is precipitated with concentrated hydrochloric acid while hot and the precipitate is filtered off with suction while cold. This gives 24 g (91%) of the title compound of m.p. 365°–370° C. (decomposition).

B10.
6,6,7-Trifluoro-6,7-dihydro-1H-[1,4]-dioxino[2,3-f]benzimidazole-2-thiol (a) A mixture of 39.5 ml of 69% nitric acid and 46 ml of 97% sulphuric acid is added dropwise at 5° C. within 1 h to 50 g of 2,2,3-trifluoro-2,3-dihydro-1,4-benzodioxine. The mixture is stirred for 1 h at 10° C., for 1 h at 20° C. and for 5 min. at 40° C., poured onto 200 g of ice and extracted with dichloromethane, and the extract is washed with water, dried with magnesium sulphate and distilled in vacuo. This gives 58 g (94%) of a mixture of 2,2,3-trifluoro-2,3-dihydro-6-nitro-(and 7-nitro)-1,4-benzodioxine of b.p. 68.5° C. (0.15 mbar) and $n_D^{20}$ 1.5080. A gas chromatogram on a 10 m fused silica column (Messrs. Chrompak) shows two peaks in the ratio 2:3.

(b) 35 g of the isomer mixture in 400 ml of ethanol are hydrogenated on 3 g of 10% palladium-on-carbon under atmospheric pressure and at 20°–30° C. in a circulating hydrogenation apparatus, and the mixture is filtered and concentrated in vacuo. This gives 30.5 g (100%) of a liquid mixture of 6-amino-(and 7-amino)-2,2,3-trifluoro-2,3-dihydro-1,4-benzodioxine.

(c) A mixture of 15.3 g of acetic anhydride and 15 ml of glacial acetic acid is added dropwise at 20°–30° C. to 28 g of the above isomer mixture, the mixture is stirred for 30 min. at 30° C., 1 ml of water is added, the mixture is stirred for 30 min. at 30° C. and the solvent is distilled off in vacuo. 19 g of a fraction of the mixture of the isomeric acetamino derivatives of m.p. 128°–133° C. is obtained by recrystallisation from toluene.

(d) 14 ml of 100% nitric acid dissolved in 60 ml of dichloromethane are added dropwise at −6° to −80° C. to 17 g of the isomer mixture of the acetamino derivatives, suspended in 200 ml of dichloromethane, and the mixture is stirred for 2 h at 0° C. and then overnight at room temperature. The mixture is poured onto 110 g of ice, and the organic phase is separated off, washed with water and concentrated in vacuo. The residue (19.8 g) is recrystallised from 20 ml of ethanol. This gives 15.5 g of a mixture of 6-acetamino-2,2,3-trifluoro-2,3-dihydro-7-nitro-1,4-benzodioxine and 7-acetamino-2,2,3-trifluoro-2,3-dihydro-6-nitro-1,4-benzodioxine.

(e) 14.5 g of the above product mixture are suspended in 80 ml of methanol and 30 ml of 5M sodium hydroxide solution are added dropwise with heating to 30° C. Stirring is continued for 0.5 h at room temperature, the mixture is poured onto 200 g of ice and 11.7 g of a mixture of 6-amino-2,2,3-trifluoro-2,3-dihydro-7-nitro-1,4-benzodioxine and 7-amino-2,2,3-trifluoro-2,3-dihydro-6-nitro-1,4-benzodioxine are obtained. A sample is separated on a silica gel column with cyclohexane/ethyl acetate (4:1) into two pure isomers of m.p. 110.5°–111.5° C. and 120°–121° C., their NMR spectra in a 60 MHz apparatus in deuterochloroform being virtually identical.

(f) 10.9 g of the above isomer mixture are hydrogenated in 300 ml of methanol at room temperature and under atmospheric pressure on 1 g of 10% palladium-on-carbon within 2.5 h. 30 ml of 4M hydrogen chloride in methanol are added, the mixture is filtered, and the residue is concentrated in vacuo and stirred with 100 ml of ether. This gives 12.6 g (98%) of 2,2,3-trifluoro-2,3-dihydro-1,4-benzodioxine-6,7-diamine dihydrochloride (m.p. >250° C.).

(g) 20.5 ml of 4M aqueous potassium hydroxide solution are added to 12 g of the above compound and 8.5 g of potassium O-ethyl dithiocarbonate (recrystallised from isopropanol) in 120 ml of ethanol and the mixture is heated to the boil under reflux for 17 h. The mixture is poured onto 300 g of ice, the pH is adjusted to 12–13 with potassium hydroxide solution, the mixture is clarified with active charcoal and the product is precipitated with concentrated hydrochloric acid. After precipitation with acid from an alkaline aqueous-alcoholic solution, 10 g (93%) of the title compound of m.p. 309°–310° C. (decomposition) are obtained.

B11.
6-Chloro-6,7,7-trifluoro-6,7-dihydro-1H-[1,4]-dioxino[2,3-f]benzimidazole-2thiol (a) A mixture of 18.3 ml of 65% nitric acid and 15.4 ml of 97% sulphuric acid is added dropwise at 5° C. to 18 g of 2-chloro-2,3,3-trifluoro-2,3-dihydro-1,4-benzodioxine, and the mixture is stirred for 2 h at 5°–10° C. and poured onto ice. The mixture is extracted with methylene chloride, and 21.3 g of a mixture of 2-chloro-2,3,3-trifluoro-2,3-dihydro-6-nitro-(and 7-nitro)-1,4-benzodioxine are obtained as an oil.

(b) Analogously to Example B10b, this gives an oily mixture of 2-chloro-2,3,3-trifluoro-2,3-dihydro-1,4-benzodioxine-6-(and 7-)amine in 95% yield, which is reacted quantitatively to a mixture of the corresponding acetamino derivatives, correspondingly to Example B10c.

(c) 19 g of the above mixture are stirred in 190 ml of dichloromethane with 16 ml of 100% nitric acid, and the reaction product is purified by chromatography on silica gel by means of cyclohexane/ethyl acetate (4:1). This gives 15 g of a mixture of 6-acetamino-2-chloro-2,3,3-trifluoro-6,7-dihydro-7-nitro-1,4-benzodioxine and 7-acetamino-2-chloro-2,3,3-trifluoro-6,7-dihydro-6-nitro-1,4-benzodioxine as a pale yellow oil.

(d) 10.2 ml of a 30% solution of sodium methylate in methanol are added dropwise at 5° C. to 14.5 g of the above mixture in 100 ml of methanol, the mixture is stirred for 1.5 h without cooling, poured onto ice, neutralised with dilute hydrochloric acid and extracted with dichloromethane and the extract is concentrated in vacuo. This gives 12.7 g of a mixture of 6-amino-2-chloro-2,3,3-trifluoro-2,3-dihydro-7-nitro-1,4-benzodioxine and 7-amino-2-chloro-2,3,3-trifluoro-2,3-dihydro-6-nitro-1,4-benzodioxine as an orange-coloured oil.

(e) 12.4 g of the above mixture are hydrogenated analogously to Example B10f. This gives 12.6 g (99%) of 2-chloro-2,3,3-trifluoro-2,3-dihydro-1,4-benzodioxine-6,7-diamine dihydrochloride.

(f) 12.4 g of the above compound are reacted analogously to Example B10g with 9.1 g of potassium O-ethyl dithiocarbonate and potassium hydroxide solution in ethanol. This gives 9.6 g (74%) of the title compound of m.p. 288°–290° C. (decomposition).

B12.
5-difluoromethoxy-4,6-dimethyl-1H-benzimidazole-2-thiol (a) Chlorodifluoromethane is passed for 7 h at 60°–70° C. into a solution of 99.7 g of 2,6-dimethylphenol and 246 g of sodium hydroxide in 500 ml of water and 500 ml of dioxane. The mixture is filtered, the filtrate is extracted with ether by shaking and the organic phase is fractionated. This gives 98 g (70%) of 1-difluoromethoxy-2,6-dimethylbenzene (b.p. 68° C./15 mbar; $n^{20}_D = 1.4631$).

(b) 113 ml of 100% nitric acid are added dropwise at 5°–10° C. to 93.9 g of the above compound in 500 ml of dichloromethane, and the mixture is stirred at room temperature overnight. The organic solution is washed with water and sodium bicarbonate solution, and concentrated. This gives 118 g (100%) of 1-difluoromethoxy-2,6-dimethyl-3-nitrobenzene ($n^{20}_D = 1.5075$).

(c) 116 g of the above compound are hydrogenated and acetylated analogously to Example B1a. This gives 99 g (81%) of (3-difluoromethoxy-2,4-dimethylphenyl)acetamide (m.p. 136°–137° C.).

(d) 20 g of the above compound are nitrated with 14.5 ml of 100% nitric acid in dichloromethane, analogously to Example B7c. This gives 21 g (89%) of N-(3-difluoromethoxy-2,4-dimethyl-6-nitrophenyl)acetamide (m.p. 184°–185° C.).

(e) 17.5 g of the above compound are stirred in 260 ml of an about 8M solution of hydrogen chloride in methanol for 12 h at 60° C., 60 ml of concentrated hydrochloric acid are added and the mixture is stirred for 18 h at 70° C. The pH is adjusted to 8 with sodium hydroxide solution, and 14.6 g (98%) of 3-difluoromethoxy-2,4-dimethyl-6-nitroaniline (m.p. 95°–96° C.) are obtained.

(f) 14 g of the above compound are hydrogenated analogously to Example B7e. This give 15.6 g (94%) of 4-difluoromethoxy-3,5-dimethyl-1,2-phenylenediamine dihydrochloride of m.p. 252° C. (decomposition).

(g) 15.6 g of the above compound are reacted analogously to Example B1e. This gives 9.8 g (71%) of the title compound (m.p. >250° C.).

B13.
4-Difluoromethoxy-5,6-dimethoxy-1H-benzimidazole-2-thiol (a) 50 g of 2,3-dimethoxyphenol are reacted analogously to Example B12a with 80 g of potassium hydroxide and chlorodifluoromethane in dioxane/water. The mixture is extracted with diisopropyl ether by shaking, the extract is washed with sodium hydroxide solution and 35 g of a product (b.p. 70°–74° C./0.3 mbar) are obtained which is reacted with 100% nitric acid analogously to Example B7b. The reaction product is subjected to chromatography on a silica gel column with cyclohexane/ethyl acetate (3:2), after which 1-difluoromethoxy-2,3-dimethoxy-5-nitrobenzene (m.p. 72°–73° C.) is isolated in 48% yield.

(b) 17 g of the above compound are hydrogenated and acetylated analogously to Example B1a. This gives 15.8 g (88%) of (3-difluoromethoxy-4,5-dimethoxyphenyl)acetamide (m.p. 104°–105° C.).

(c) 10 g of the above compound are stirred in 120 ml of dichloromethane with 5.1 ml of 100% nitric acid for 1 h at 0° C. This given 10.1 g (86%) of N-(3-difluoromethoxy-4,5-dimethoxy-2-nitrophenyl)acetamide (m.p. 144°–145° C.).

(d) 8.3 g of the above compound are stirred with 47 ml of concentrated hydrochloric acid and 120 ml of methanol for 1.5 h at 70° C. The mixture is neutralised and extracted with dichloromethane, and the product is allowed to crystallise from toluene. This gives 5.7 g (80%) of 3-difluoromethoxy-4,5-dimethoxy-2-nitroaniline (m.p. 141°–142° C.).

(e) Analogously to Example B7e, the above compound gives 3-difluoromethoxy-4,5-dimethoxy-1,2-phenylenediamine dihydrochloride of m.p. 233°–234° C. (decomposition) in 92% yield.

(f) Analogously to Example B1e, the above compound gives the title compound (m.p. 223°–224° C.) in 84% yield.

B14.
5-Difluoromethoxy-6-methyl-1H-benzimidazole-2-thiol (a) Analogously to Example B12, 2-methylphenol and chlorodifluoromethane gives 1-difluoromethoxy-2-methylbenzene (b.p. 45°–47° C./11–12 mbar) in 51% yield and the latter gives with 100% nitric acid a mixture of 1-difluoromethoxy-2-methyl-4-nitrobenzene and 1-difluoromethoxy-2-methyl-5-nitrobenzene (b.p. 70°–74° C./1–1.5 mbar; 80% yield), which mixture is reduced, acetylated and nitrated. The crude product is recrystallised from ethanol. This gives N-(4-difluoromethoxy-5-methyl-2-nitrophenyl)acetamide (m.p. 96°–97° C.) in 42% yield.

(b) 110.4 g of the above compound are treated in 1.6 l of methanol at 10°–25° C. with 84 g of 30% sodium methylate in methanol, and the mixture is poured onto ice after 1 h. This gives 82.5 g (89%) of 4-difluoromethoxy-5-methyl-2-nitroaniline (m.p. 73°–74° C.).

(c) 82 g of the above compound are hydrogenated in 400 ml of ethanol on palladium-on-carbon, and the filtered solution of 4-difluoromethoxy-5-methyl-1,2-phenylenediamine is heated for 15 h under reflux with 82.4 g of potassium O-ethyl dithiocarbonate and 70 ml of water and is worked up analogously to B1e. This gives 71 g (82%) of the title compound of m.p. 327°–329° C. (from ethanol).

B15.
5-(2-Chloro-1,1,2-trifluoroethoxy)-1H-benzimidazole-2-thiol 120 g of N-[4-(2-chloro-1,1,2-trifluoroethoxy)phenyl]acetamide are nitrated analogously to B1 to give N-[4-(2-chloro-1,1,2-trifluoroethoxy)-2-nitrophenyl]acetamide (96%, slowly crystallising oil) and deacetylated analogously to B14b to give 4-(2-chloro-1,1,2-trifluoroethoxy)-2-nitroaniline (96%, m.p. 65°–66° C.). Analogously to B14c, the title compound of m.p. 297°–298° C.

(from toluene) is obtained in 90% yield via 4-(2-chloro-1,1,2-trifluoroethoxy)-1,2-phenylenediamine.

Commercial usefulness

The compounds of the formula I according to the invention and their salts have valuable pharmacological properties which render them commercially useful. They markedly inhibit the secretion of gastric acid in warm-blooded animals and, furthermore, exhibit an excellent protective action on the stomach and intestines of warm-blooded animals. This protective action on the stomach and intestines is in some cases observed even when doses are administered which are below the doses which inhibit the secretion of acid. In addition, the compounds according to the invention are distinguished by the absence of significant side effects and by a wide therapeutic range. A further aspect essential to the invention is that the compounds of the formula I have a high chemical stability and a significant activity maximum in the particular desired pH range.

"Protection of the stomach and intestines" is understood in this connection as the prevention and treatment of gastro-intestinal diseases, in particular gastro-intestinal inflammatory diseases and lesions (such as, for example Ulcus ventriculi, Ulcus duodeni, gastritis and irritable stomach due to hyperacidity or medicaments) which can be caused, for example, by microorganisms, bacterial toxins, medicaments (for example certain antiphlogistics and antirheumatics), chemicals (for example ethanol), gastric acid or stress situations.

With their excellent properties, the compounds according to the invention surprisingly prove to be markedly superior to the compounds known from the state of the art. Owing to these properties, the compounds according to the invention and their pharmacologically acceptable salts are outstandingly suitable for use in human and veterinary medicine, being used especially for the treatment and prophylaxis of diseases of the stomach and intestines and of those diseases which are caused by an excessive secretion of gastric acid. In addition, the high storage stability of the compounds according to the invention allows their use in pharmaceutical preparations without any problems.

The invention also relates to the compounds according to the invention for use in the treatment and prophylaxis of the abovementioned diseases.

Likewise, the invention comprises the use of the compounds according to the invention in the preparation of medicaments which are employed for the treatment and prophylaxis of the abovementioned diseases.

Furthermore, the invention relates to medicaments which contain one or more compounds of the formula I according to the invention and/or pharmacologically acceptable salts thereof.

The medicaments are prepared by processes which are known per se and are familiar to an expert. As medicaments, the pharmacologically active compounds (=active ingredients) accordingly to the invention are employed as such or, preferably, in combination with suitable pharmaceutical auxiliaries in the form of tablets, coated tablets, capsules, suppositories, plasters (for example as TTS), emulsions, suspensions or solutions, the content of active compound advantageously being between 0.1 and 95%.

An expert is familiar with the auxiliaries which are suitable for the desired medicament formulations on the basis of his expert knowledge. In addition to solvents, gelling agents, suppository bases, tabletting auxiliaries and other active compound excipients, it is possible to use, for example, antioxidants, dispersing agents, emulsifiers, antifoaming agents, flavour correctants, preservatives, solubilisers, dyestuffs or, in particular, permeation promoters and complexing agents (for example cyclodextrins).

The active compounds can be administered orally, parenterally or percutaneously.

In general, it has proved advantageous in human medicine to administer the active compound or compounds, when these are administered orally, in a daily dose of about 0.05 to about 50, preferably 0.25 to 20, in particular 0.5 to 10, mg/kg of body weight, if desired in the form of several, preferably 1 to 4, individual doses, to achieve the desired result. In the case of parenteral treatment, similar or (especially when the active compounds are administered intravenously) as a rule lower doses can be used. The particular optimum dosage required and the mode of administration of the active compounds can easily be determined by any expert on the basis of his expert knowledge.

If the compounds according to the invention and/or their salts are to be employed for the treatment of the abovementioned diseases, the pharmaceutical formulations can also contain one or more pharmacologically active constituents from other groups of medicaments, such as antacids, for example aluminium hydroxide and magnesium aluminate, tranquillisers such as benzodiazepines, for example diazepam, spasmolytics, such as, for example, bietamiverine and camylofin, anticholinergics such as, for example, oxyphencyclimine and phencarbamide, local anaesthetics such as, for example, tetracaine and procaine, and if appropriate also ferments, vitamins or aminoacids.

In this connection, especially the combination of the compounds according to the invention with other pharmaceuticals which inhibit the secretion of acid should be singled out, such as, for example, $H_2$ blockers (for example cimetidine and ranitidine), and also with so-called peripheral anticholinergics (for example pirenzepine, telenzepine and zolenzepine) and with gastrin antagonists, with the object of boosting the main action in an additive or hyper-additive direction and/or to eliminate or reduce the side effects.

Pharmacology

The excellent protective action of the compounds according to the invention on the stomach and the action inhibiting gastric secretion can be demonstrated by animal experiments on Shay rats as a model. The investigated compounds according to the invention have been given numbers as follows:

| Serial No. | Name of the compound |
|---|---|
| 1 | 5-Difluoromethoxy-2-[(4-methoxy-3-methyl-2-pyridyl)methylsulphinyl]-4,6-dimethyl-1H-benzimidazole |
| 2 | 5-Difluoromethoxy-6-methoxy-2-{[1-(4-methoxy-2-pyridyl)ethyl]sulphinyl}-1H-benzimidazole |
| 3 | 5-(1,1,2,2-Tetrafluoroethoxy)-2-{[1-(4-methoxy-2-pyridyl)ethyl]sulphinyl}-1H-benzimidazole |
| 4 | 5-Difluoromethoxy-2-[(3,4-dimethoxy-2-pyridyl)methylsulphinyl]-4,6-dimethyl-1H-benzimidazole |
| 5 | 2,2-Difluoro-6-{[1-(4-methoxy-2-pyridyl)ethyl]sulphinyl}-5H-[1,3]-dioxolo[4,5-f]benzimidazole |
| 6 | 5-(2-Chloro-1,1,2-trifluoroethoxy)-2-[(4-methoxy-2-pyridyl)methylsulphinyl]-1H-benzimidazole |

-continued

| Serial No. | Name of the compound |
|---|---|
| 7 | 5-(2-Chloro-1,1,1-trifluoroethoxy)-2-{[1-(4-methoxy-2-pyridyl)ethyl]sulphinyl}-1H-benzimidazole |
| 8 | 5-Difluoromethoxy-2-[(4-methoxy-3-methyl-2-pyridyl)methylthio]-4,6-dimethyl-1H-benzimidazole |
| 9 | 5-Difluoromethoxy-6-methoxy-2-{[1-(4-methoxy-2-pyridyl)ethyl]thio}-1H-benzimidazole |
| 10 | 5-(2-Chloro-1,1,2-trifluoroethoxy)-2-[(4-methoxy-3-methyl-2-pyridyl)methylsulphinyl]-1H-benzimidazole |

The effects of the investigated compounds on the formation of stomach lesions induced by pylorus ligature and oral administration of 100 mg/kg of acetylsalicylic acid and the gastric secretion (HCl) for 4 h in rats (so-called Shay rats) are shown in the table which follows.

Protective action on the stomach and inhibition of gastric secretion

| Serial No. | Protective action on the stomach (rats), inhibition of the lesion index, ED50+ [mg/kg, orally] | Inhibition of the HCl secretion of the stomach (rats; total 4 h) | | |
|---|---|---|---|---|
| | | % inhibition of the HCl secretion ++ | ED25+ [mg/kg, orally] | ED50+ [mg/kg, orally] |
| 1 | 0.50 | 22 | 0.50 | 1.1 |
| 2 | 0.60 | ~20 | ~1 | ~2 |
| 3 | 0.50 | 35 | 0.35 | 0.8 |
| 4 | ~1 | 10 | ~1.3 | ~2 |
| 5 | 1 | 25 | 1 | 1.7 |
| 6 | 0.55 | 25 | 0.55 | 1.3 |
| 7 | 0.6 | 40 | 0.4 | 0.8 |
| 8 | 0.7 | 15 | 1 | 1 |
| 9 | 1.7 | 35 | <1 | ~4 |
| 10 | 0.4 | 27 | 0.4 | 0.8 |

+ ED25 and ED50 = dose which reduces the lesion index and the HCl secretion (Σ4 h) of the rat stomach in the treated group by 25 and 50% respectively, as compared with the control group.
++ after administration of the anti-ulcer ED50

The anti-ulcerogenic action was tested by the method of so-called Shay rats:

The ulcers are provoked in rats (female, 180-200 g, 4 animals in each cage on a high grid) kept fasting for 24 hours by pylorus ligature (under diethyl ether anaesthesia) and oral administration of 100 mg/10 ml/kg of acetylsalicylic acid. The substances to be tested are administered orally (10 ml/kg) one hour before the pylorus ligature. The wounds are closed by means of Michel clamps. 4 hours later, the animals are killed under ether intoxication by atlas dislocation and the stomach is resected. The stomach is opened longitudinally and fixed on a cork plate, after first determining the quantity of the secreted gastric juice (volume) and later its HCl content (titration with sodium hydroxide solution); the number and size (=diameter) of existing ulcers was determined by means of a stereomicroscope at 10-fold magnification. The product of the degree of severity (according to the points rating below) and of the number of ulcers is used as the individual lesion index.

| Points rating: | | |
|---|---|---|
| no ulcers | | 0 |
| ulcer diameter | 0.1-1.4 mm | 1 |
| | 1.5-2.4 mm | 2 |
| | 2.5-3.4 mm | 3 |
| | 3.5-4.4 mm | 4 |
| | 4.5-5.4 mm | 5 |
| | >5.5 mm | 6 |

The reduction in the mean lesion index of each treated group as compared with that of the control group (=100%) is taken as the measure of the anti-ulcerogenic effect. ED25 and ED50 designate those doses which reduce the mean lesion index and the HCl secretion by 25% and 50% respectively, as compared with the control.

Toxicity

The LD50 of all the compounds tested is above 1000 mg/kg [orally] in mice.

We claim:
1. A compound of formula I

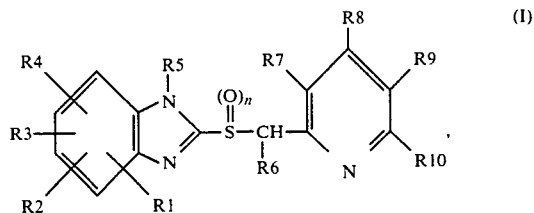

wherein each of R1, R2, R3 and R4 is in any position in the benzo part of the benzimidazole and wherein R1 denotes hydrogen or $C_1$-$C_6$-alkyl, R2 denotes hydrogen, halogen, $C_1$-$C_6$-alkyl, $C_1$-$C_6$-alkoxy, $C_1$-$C_4$-alkoxy-$C_1$-$C_4$-alkyl, $C_1$-$C_4$-alkoxy-$C_1$-$C_4$-alkoxy, phenyl, phenoxy, phenoxy-$C_1$-$C_4$-alkyl, phenoxy-$C_1$-$C_4$-alkoxy, phen-$C_1$-$C_4$-alkyl or phen-$C_1$-$C_4$-alkoxy, R3 denotes hydrogen, $C_1$-$C_6$-alkyl, $C_1$-$C_6$-alkoxy, $C_1$-$C_4$-alkoxy wholly or predominantly substituted by fluorine, chlorodifluoromethoxy or 2-chloro-1,1,2-trifluoroethoxy or, together with R4, denotes $C_1$-$C_2$-alkylenedioxy wholly or partially substituted by fluorine, or chlorotrifluoroethylenedioxy, R4 denotes $C_1$-$C_4$-alkoxy wholly or predominantly substituted by fluorine, chlorodifluoromethoxy or 2-chloro-1,1,2-trifluoroethoxy or, together with R3, denotes $C_1$-$C_2$-alkylenedioxy wholly or partially substituted by fluorine, or chlorotrifluoroethylenedioxy, R5 denotes hydrogen or a group which can readily be eliminated under physiological conditions, R6 denotes hydrogen or $C_1$-$C_4$-alkyl, R7 denotes hydrogen, $C_1$-$C_6$-alkyl or $C_1$-$C_6$-alkoxy, R8 denotes hydrogen, $C_1$-$C_6$-alkyl, $C_1$-$C_6$-alkoxy, $C_1$-$C_4$-alkoxy-$C_1$-$C_4$-alkoxy, $C_2$-$C_5$-alkenyloxy or $C_2$-$C_5$-alkynyloxy, R9 denotes hydrogen or $C_1$-$C_6$-alkyl or $C_1$-$C_6$-alkoxy, R10 denotes hydrogen or $C_1$-$C_6$-alkyl, and n represents the numbers 0 or 1, or a salt thereof, with the proviso that:
(a) R1 denotes hydrogen at the 4- or 7-position of the benzimidazole ring,
(b) R2, when at the 5- or 6-position of the benzimidazole ring, is $C_1$-$C_4$-alkoxy-$C_1$-$C_4$-alkyl, $C_1$-$C_6$-alkoxy-$C_1$-$C_4$-alkoxy, phenyl, phenoxy, phenoxy-$C_1$-$C_4$-alkyl, phenoxy-$C_1$-$C_4$-alkoxy, phen-$C_1$-$C_4$-alkyl or phen-$C_1$-$C_4$-alkoxy, and
(c) R3, when at the 5- or 6-position of the benzimidazole ring, is 2-chloro-1,1,2-trifluoroethoxy, when
(d) R4 is at the 5- or 6-position and denotes chlorodifluoromethoxy or $C_1$-$C_4$-alkoxy wholly or predominantly substituted by fluorine, and
(e) R5 denotes hydrogen, and
(f) R6 denotes hydrogen, and
(g) R7 denotes hydrogen or $C_1$-$C_6$-alkyl or $C_1$-$C_6$-alkoxy, and
(h) R8 denotes hydrogen or $C_1$-$C_6$-alkyl or $C_1$-$C_6$-alkoxy, and
(i) R9 denotes hydrogen or $C_1$-$C_6$-alkyl or $C_1$-$C_6$-alkoxy, and
(j) R10 denotes hydrogen, and
(k) hydrogen atoms are present at the 4- and 7-positions of the benzimidazole ring, and
with the further proviso that:
(l) R3 and R4 (when in the 5- and 6-positions) do not together denote $C_1$-$C_2$-alkylenedioxy wholly or partially substituted by fluorine, or chlorotrifluoroethylenedioxy,
when
(m) R5 denotes hydrogen, and
(n) R6 denotes hydrogen, and
(o) R7 denotes hydrogen or $C_1$-$C_6$-alkyl or $C_1$-$C_6$-alkoxy, and
(p) R8 denotes hydrogen or $C_1$-$C_6$-alkyl or $C_1$-$C_6$-alkoxy, and
(q) R9 denotes hydrogen or $C_1$-$C_6$-alkyl or $C_1$-$C_6$-alkoxy, and
(r) R10 denotes hydrogen, and
(s) hydrogen atoms are present at the 4- and 7-positions of the benzimidazole ring.

2. A compound of formula I according to claim 1, wherein
R1, R2, R3 and R4 can be in any desired positions in the benzo part of the benzimidazole and wherein
R1 denotes hydrogen or $C_1$-$C_6$-alkyl,
R2 denotes hydrogen, halogen, $C_1$-$C_6$-alkyl, $C_1$-$C_6$-alkoxy, $C_1$-$C_4$-alkoxy-$C_1$-$C_4$-alkyl, $C_1$-$C_4$-alkoxy-$C_1$-$C_4$-alkoxy, phenyl, phenoxy, phenoxy-$C_1$-$C_4$-alkyl, phenoxy-$C_1$-$C_4$-alkoxy, phen-$C_1$-$C_4$-alkyl or phen-$C_1$-$C_4$-alkoxy,
R3 denotes hydrogen, $C_1$-$C_6$-alkyl, $C_1$-$C_6$-alkoxy, $C_1$-$C_4$-alkoxy wholly or predominantly substituted by fluorine, chlorodifluoromethoxy or 2-chloro-1,1,2-trifluoroethoxy or, together with R4, denotes $C_1$-$C_2$-alkylenedioxy wholly or partially substituted by fluorine, or chlorotrifluoroethylenedioxy,
R4 denotes $C_1$-$C_4$-alkoxy wholly or predominantly substituted by fluorine, chlorodifluoromethoxy or 2-chloro-1,1,2-trifluoroethoxy or, together with R3, denotes $C_1$-$C_2$-alkylenedioxy wholly or partially substituted by fluorine, or chlorotrifluoroethylenedioxy,
R5 denotes hydrogen or a group which can readily be eliminated under physiological conditions,
R6 denotes hydrogen or $C_1$-$C_4$-alkyl,
R7 denotes hydrogen or $C_1$-$C_6$-alkyl and
R8 denotes hydrogen, $C_1$-$C_6$-alkyl, $C_1$-$C_6$-alkoxy, $C_1$-$C_4$-alkoxy-$C_1$-$C_4$-alkoxy, $C_2$-$C_5$-alkenyloxy or $C_2$-$C_5$-alkynyloxy,
R9 denotes hydrogen or $C_1$-$C_6$-alkyl,
R10 denotes hydrogen or $C_1$-$C_6$-alkyl and
n represents the numbers 0 or 1,
or a salt thereof.

3. A compound of formula I according to claim 1, wherein
R1, R2, R3 and R4 can be in any desired positions in the benzo part of the benzimidazole and wherein
R1 denotes hydrogen or $C_1$-$C_6$-alkyl,
R2 denotes hydrogen, halogen, $C_1$-$C_6$-alkyl, $C_1$-$C_6$-alkoxy, $C_1$-$C_4$-alkoxy-$C_1$-$C_4$-alkyl, $C_1$-$C_4$-alkoxy-$C_1$-$C_4$-alkoxy, phenyl, phenoxy, phenoxy-$C_1$-$C_4$-alkyl, phenoxy-$C_1$-$C_4$-alkoxy, phen-$C_1$-$C_4$-alkyl or phen-$C_1$-$C_4$-alkoxy,
R3 denotes hydrogen, $C_1$-$C_6$-alkyl, $C_1$-$C_6$-alkoxy, $C_1$-$C_4$-alkoxy wholly or predominantly substituted by fluorine, chlorodifluoromethoxy or 2-chloro-1,1,2-trifluoroethoxy or, together with R4, denotes $C_1$-$C_2$-alkylenedioxy wholly or partially substituted by fluorine, or chlorotrifluoroethylenedioxy,
R4 denotes $C_1$-$C_4$-alkoxy wholly or predominantly substituted by fluorine, chlorodifluoromethoxy or 2-chloro-1,1,2-trifluoroethoxy or, together with R3, denotes $C_1$-$C_2$-alkylenedioxy wholly or partially substituted by fluorine, or chlorotrifluoroethylenedioxy,
R5 denotes hydrogen or a group which can readily be eliminated under physiological conditions,
R6 denotes hydrogen or $C_1$-$C_6$-alkyl,
R8 denotes hydrogen, $C_1$-$C_6$-alkyl, $C_1$-$C_6$-alkoxy, $C_1$-$C_4$-alkoxy-$C_1$-$C_4$-alkoxy, $C_2$-$C_5$-alkenyloxy or $C_2$-$C_5$-alkynyloxy,
one of the substituents R7 and R9 denotes $C_1$-$C_6$-alkoxy and the other denotes hydrogen, $C_1$-$C_6$-alkyl or $C_1$-$C_6$-alkoxy,
R10 denotes hydrogen or $C_1$-$C_6$-alkyl and
n represents the numbers of 0 or 1,
or a salt thereof.

4. A compound of formula I according to claim 1 or 2 or 3, wherein R6 denotes hydrogen and R10 denotes hydrogen and R1, R2, R3, R4, R5, R7, R8, R9 and n have the meanings given in claims 1 or 2 or 3, or a salt thereof.

5. A compound of formula I according to claim 1 or 2 or 3, wherein R6 denotes $C_1$-$C_4$-alkyl and R10 denotes hydrogen and R1, R2, R3, R4, R5, R7, R8, R9 and n have the meanings given in claims 1 or 2 or 3, or a salt thereof.

6. A compound of formula I according to claim 1, wherein
R1 denotes hydrogen, methyl or ethyl,
R2 denotes hydrogen, chlorine, fluorine, methyl, ethyl, methoxy or ethoxy,
R3 denotes hydrogen, methyl, ethyl, methoxy, ethoxy, 1,1,2,2-tetrafluoroethoxy, trifluoromethoxy, 2,2,2-trifluoroethoxy, difluoromethoxy or 2-chloro-1,1,2-trifluoroethoxy or, together with R4, denotes difluoromethylenedioxy, 1,1,2-trifluoroethylenedioxy or 1-chloro-1,2,2-trifluoroethylenedioxy,
R4 denotes 1,1,2,2-tetrafluoroethoxy, trifluoromethoxy, 2,2,2-trifluoroethoxy, difluoromethoxy or 2-chloro-1,1,2-trifluoroethoxy or, together with R3, denotes difluoromethylenedioxy, 1,1,2-trifluoroethylenedioxy or 1-chloro-1,2,2-trifluoroethylenedioxy,
R5 denotes hydrogen,
R6 denotes hydrogen, methyl or ethyl,
R7 denotes hydrogen, methyl, ethyl, methoxy or ethoxy,
R8 denotes hydrogen, methyl, ethyl, methoxy, ethoxy or allyloxy,
R9 denotes hydrogen, methyl, ethyl, methoxy or ethoxy,
R10 denotes hydrogen, methyl or ethyl and
n represents the numbers 0 or 1, or a salt thereof.

7. A compound of formula I according to claim 1, wherein
R1 denotes hydrogen, methyl or ethyl,
R2 denotes hydrogen, chlorine, fluorine, methyl, ethyl, methoxy or ethoxy,
R3 denotes hydrogen, methyl, ethyl, methoxy, ethoxy, 1,1,2,2-tetrafluoroethoxy, trifluoromethoxy, 2,2,2-trifluoroethoxy, difluoromethoxy or 2-chloro-1,1,2-trifluoroethoxy or, together with R4, denotes difluoromethylenedioxy, 1,1,2-trifluoroethylenedioxy or 1-chloro-1,2,2-trifluoroethylenedioxy,
R4 denotes 1,1,2,2-tetrafluoroethoxy, trifluoromethoxy, 2,2,2-trifluoroethoxy, difluoromethoxy or 2-chloro-1,1,2-trifluoroethoxy or, together with R3, denotes difluoromethylenedioxy, 1,2,2-trifluoroethylenedioxy or 1-chloro-1,2,2-trifluoroethylenedioxy,
R5 denotes hydrogen,
R6 denotes hydrogen, methyl or ethyl,
R7 denotes hydrogen, methyl or ethyl,
R8 denotes hydrogen, methyl, ethyl, methoxy, ethoxy or allyloxy,
R9 denotes hydrogen, methyl or ethyl,
R10 denotes hydrogen, methyl or ethyl and
n represents the numbers 0 or 1,
or a salt thereof.

8. A compound of formula I according to claim 1, wherein
R1 denotes hydrogen, methyl or ethyl,
R2 denotes hydrogen, chlorine, fluorine, methyl, ethyl, methoxy or ethoxy,
R3 denotes hydrogen, methyl, ethyl, methoxy, ethoxy, 1,1,2,2-tetrafluoroethoxy, trifluoromethoxy, 2,2,2-trifluoroethoxy, difluoromethoxy or 2-chloro-1,1,2-trifluoroethoxy or, together with R4, denotes difluoromethylenedioxy, 1,1,2-trifluoroethylenedioxy or 1-chloro-1,2,2-trifluoroethylenedioxy,
R4 denotes 1,1,2,2-tetrafluoroethoxy, trifluoromethoxy, 2,2,2-trifluoroethoxy, difluoromethoxy or 2-chloro-1,1,2-trifluoroethoxy or, together with R3, denotes difluoromethylenedioxy, 1,1,2-trifluoroethylenedioxy or 1-chloro-1,2,2-trifluoroethylenedioxy,
R5 denotes hydrogen,
R6 denotes hydrogen, methyl or ethyl,
R8 denotes hydrogen, methyl, ethyl, methoxy, ethoxy or allyloxy,
one of the substituents R7 and R9 denotes methoxy or ethoxy and the other denotes hydrogen, methyl, ethyl, methoxy or ethoxy,
R10 denotes hydrogen, methyl or ethyl and
n represents the numbers 0 or 1,
or a salt thereof.

9. A compound of formula I according to claim 6 or 7 or 8, in which R6 denotes hydrogen and R10 denotes hydrogen.

10. A compound of formula I according to claim 6 or 7 or 8, in which R6 denotes methyl or ethyl and R10 denotes hydrogen.

11. A compound of formula I according to claim 1, wherein
R1 denotes hydrogen,
R2 denotes hydrogen, methyl or methoxy,
R3 denotes hydrogen, methyl, methoxy, 1,1,2,2-tetrafluoroethoxy, difluoromethoxy or 2-chloro-1,1,2-trifluoroethoxy or, together with R4, denotes difluoromethylenedioxy,
R4 denotes 1,1,2,2-tetrafluoroethoxy, difluoromethoxy or 2-chloro-1,1,2-trifluoroethoxy or, together with R3, denotes difluoromethylenedioxy,
R5 denotes hydrogen,
R6 denotes hydrogen or methyl,
R7 denotes hydrogen, methyl or methoxy,
R8 denotes methoxy,
R9 denotes hydrogen,
R10 denotes hydrogen and
n represents the numbers 0 or 1,
and the salts.

12. A compound selected from the group consisting of
5-difluoromethoxy-2-[(4-methoxy-3-methyl-2-pyridyl)methylsulphinyl]-4,6-dimethyl-1H-benzimidazole,
5-difluoromethoxy-6-methoxy-2-{[1-(4-methoxy-2-pyridyl)ethyl]sulphinyl}-1H-benzimidazole,
5-(1,1,2,2-tetrafluoroethoxy)-2-{[1-(4-methoxy-2-pyridyl)ethyl]sulphinyl}-1H-benzimidazole,
5-difluoromethoxy-2[(3,4-dimethoxy-2-pyridyl)methylsulphinyl]-4,6-dimethyl-1H-benzimidazole,
2,2-difluoro-6-{[1-(4-methoxy-2-pyridyl)ethyl]sulphinyl}-5H-[1,3]-dioxolo[4,5-]benzimidazole,
5-(2-chloro-1,1,2-trifluoroethoxy)-2-[(4-methoxy-2-pyridyl)methylsulphinyl]-1H-benzimidazole,
5-(2-chloro-1,1,1-trifluoroethoxy)-2-{[1-(4-methoxy-2-pyridyl)ethyl]sulphinyl}-1H-benzimidazole,
5-difluoromethoxy-2-[(4-methoxy-3-methyl-2-pyridyl)methylthio]-4,6-dimethyl-1H-benzimidazole,
5-difluoromethoxy-6-methoxy-2-{[1-(4-methoxy-2-pyridyl)ethyl]thio}-1H-benzimidazole,
5-(2-Chloro-1,1,2-trifluoroethoxy)-2-[(4-methoxy-3-methyl-2-pyridyl)methylsulphinyl]-1H-benzimidazole
or a pharmacologically acceptable salt of one of these compounds.

13. A compound according to claim 1 or 2 or 3 wherein R6 denotes hydrogen.

14. A compound according to claim 1 or 2 or 3 wherein R6 denotes $C_1$–$C_4$-alkyl.

15. A compound according to claim 6 or 7 or 8 wherein R6 denotes hydrogen.

16. A compound according to claim 6 or 7 or 8 wherein R6 denotes methyl or ethyl.

17. A compound according to claim 11 wherein R6 denotes hydrogen.

18. A compound according to claim 11 wherein R6 denotes methyl.

19. A compound according to claim 1 wherein R5 denotes hydrogen.

20. A compound according to claim 1 which is 5-(1,1,2,2-tetrafluoroethoxy)-2-{[1-(4-methoxy-2-pyridyl)ethyl]sulphinyl}-1H-benzimidazole or a pharmacologically-compatible salt thereof.

21. A medicament composition useful for the treatment and/or prophylaxis of a disease of the stomach and/or intestines or of a disease based on increased secretion of gastric acid and containing at least one pharmaceutical auxiliary and an effective amount of a compound according to one of claims 2 to 12 or 1 and/or a pharmacologically-acceptable salt thereof.

22. In the preparation of a medicament composition having a suitable pharmaceutical auxiliary and an active ingredient which is useful for the treatment and/or prophylaxis of a disease of the stomach and/or intestines or of a disease based on increased secretion of gastric acid, the improvement wherein the active ingredient is a compound according to one of claims 2 to 12 or 1 or a pharmacologically-acceptable salt thereof.

23. In the treatment and/or prophylaxis of a disease of the stomach and/or intestines or of a disease based on increased secretion of gastric acid, a process which comprises administering to a patient afflicted with or subject to discomfort from such disease an effective amount of a compound according to one of claims 2 to 12 or 1 or of a pharmacologically-acceptable salt thereof.

* * * * *